United States Patent [19]

Vandehey

[11] Patent Number: 4,919,144
[45] Date of Patent: Apr. 24, 1990

[54] DEFIBRILLATOR ECG INTERPRETER

[75] Inventor: Marvin E. Vandehey, Seattle, Wash.

[73] Assignee: First Medic, Bellevue, Wash.

[21] Appl. No.: 161,062

[22] Filed: Feb. 26, 1988

[51] Int. Cl.$^5$ .............................................. A61B 5/04
[52] U.S. Cl. .................................... 128/705; 128/702; 128/903
[58] Field of Search ............... 128/903, 702, 703, 704, 128/705, 708, 419 PG, 419 D; 364/413.06

[56] References Cited

U.S. PATENT DOCUMENTS

| 4,360,030 | 11/1982 | Citron et al. | 128/702 |
| 4,523,595 | 6/1985 | Zibell | 128/419 D |
| 4,574,810 | 3/1986 | Lerman | 128/419 D |
| 4,583,553 | 4/1986 | Shah et al. | 128/708 |
| 4,619,265 | 10/1986 | Morgan et al. | 128/419 D |
| 4,635,639 | 1/1987 | Hakala et al. | 128/419 D |
| 4,796,620 | 1/1989 | Imran | 128/419 D |

Primary Examiner—Francis Jaworski
Assistant Examiner—George Manuel
Attorney, Agent, or Firm—Seed and Berry

[57] ABSTRACT

A defibrillator electrocardiogram (ECG) interpreter for indicating whether to treat a patient with a defibrillator. A sequence of digitized samples from a patient's ECG is periodically tested to identify asystole, noise, no-treat and treat conditions. A single result then is stored for each period. The treat result occurs when a patient is experiencing ventricular fibrillation or high rate ventricular tachycardia. The current result and up to two of the results corresponding to immediately previous ECG sample periods are then compared to derive a system output. In an automatic defibrillator embodiment, the system output causes defibrillation automatically for a treat output. In a semiautomatic defibrillator embodiment, the system output causes a message to be presented to an operator. The operator then makes the decision whether to defibrillate based upon the system output.

30 Claims, 21 Drawing Sheets 4,919,144

DEFIBRILLATOR ECG INTERPRETER

TECHNICAL FIELD

This invention relates to a method and an apparatus for automatically analyzing electrocardiograph (ECG) signals to determine whether to treat a patient with a defibrillator. More particularly, this invention relates to a method and an apparatus for automatically analyzing ECG signals to determine the presence of asystole, noise, no-treat and treat conditions.

BACKGROUND ART

A defibrillator is an electronic device that applies a short high voltage pulse to the heart by means of electrodes placed on the chest wall. It is used to restore a more desirable rhythm to a heart experiencing ventricular fibrillation, ventricular tachycardia, or other abnormal heartbeat patterns. Ventricular fibrillation is rapid erratic contractions of the muscle fibers of the ventricles that do not result in coordinated contractions of the ventricles. Ventricular tachycardia is an abnormally rapid heartbeat generated by excitation within the ventricles.

To determine if defibrillation is required, most defibrillators have, in the past, relied on manual interpretation of ECG signals displayed on an ECG monitor or plotted on a strip of paper. In such systems, the ECG signal is displayed as a waveform normally containing the P and T waves, as well as the QRS peaks associated with ventricular contraction. The operator interprets the sometimes noisy waveform to determine the presence of ventricular fibrillation, ventricular tachycardia, asystole (the absence of contractions of the heart), or other abnormal heartbeat patterns. The operator must be highly trained in order to manually interpret the ECG signals with the degree of accuracy necessary to base a decision to defibrillate on his or her interpretation. Manual ECG interpretation has thus worked adequately in hospitals where equipment and trained personnel are readily available. Increasingly, however, defibrillators are being used outside the hospital by relatively untrained individuals such as paramedics, emergency medical technicians, firemen, policemen, and other individuals who respond to an emergency on the scene.

The recently introduced automatic and semiautomatic defibrillators eliminate the requirement of manual ECG interpretation by having microprocessors or other electronic hardware perform the ECG interpretation. An automatic defibrillator interprets ECG signals, makes a decision whether to treat (defibrillate) a patient, and then, when the decision is to treat, automatically defibrillates the patient. A semiautomatic defibrillator interprets ECG signals and makes the decision whether to treat the patient, but then presents the decision on a display or other means to an operator. The operator then initiates the defibrillation according to the decision.

DISCLOSURE OF THE INVENTION

An object of this invention is to provide an interpreter of ECG signals that reliably distinguishes asystole, noise, no-treat and treat conditions, where treat conditions are interpreted to be ventricular fibrillation or ventricular tachycardia having rates above 180 beats per minute (bpm).

Another object of this invention is to provide a microprocessor-based ECG interpreter.

Still another object of this invention is to provide a data processing method for generating an output signal indicating whether to treat a patient with a defibrillator.

These and other objects of the invention are provided by an interpreter that processes sequences of ECG samples. Periodically, a block of sequential ECG samples is digitally filtered to derive noise reduced samples, noise samples, derivatives of noise reduced samples, a moving average of the absolute value of the derivatives, local maxima and minima of the derivative values, and local minima and minima of the noise reduced samples. Select variables are then derived from the digital filter outputs and the sequence of ECG samples.

During each of successive periods, tests are executed to determine the presence of asystole, noise, no-treat conditions and treat conditions. A single result of any one of asystole, noise, no-treat or treat is tallied for each period. Asystole can be alternatively chosen to be regarded as a treat condition or a no-treat condition. The results of up to a first predetermined number of successive periods are polled to derive a system output. When at least a second predetermined number of noise results are present, "noise" is the system output. When at least the second predetermined number of no-treat results are present, "no-treat" is the system output. When at least the second predetermined number of treat results are present, "treat" is the system output.

In one aspect, the invention is a system for detecting ventricular fibrillation and high rate ventricular tachycardia in the electrocardiogram (ECG) of a patient. The system comprises input means for receiving a sequence of digitized ECG samples of the ECG signal of the patient and storage means for storing the sequence of digitized ECG samples received through the input means. The system also comprises processing means for detecting noise, patient heart action that should be defibrillated, or patient heart action that should not be defibrillated in said sequence of digitized ECG samples stored in the storage means. Finally, the system comprises output means connected to the processing means for indicating when the processing means detects ventricular fibrillation or high rate ventricular tachycardia.

In another aspect, the invention is a data processing method for generating an output signal indicating whether to treat a patient with a defibrillator. The data processing method is implemented by processing means periodically receiving a sequence of digitally filtered ECG samples of the patient's ECG signal and comprises the steps of testing the sequence of digitally filtered ECG samples for asystole, testing the sequence of digitally filtered ECG samples for noise, and testing the sequence of digitally filtered ECG samples for patient heart action that should be defibrillated, or patient heart action that should not be defibrillated, including low rate ventricular tachycardia.

BEST MODE FOR CARRYING OUT THE INVENTION

Figure 1:
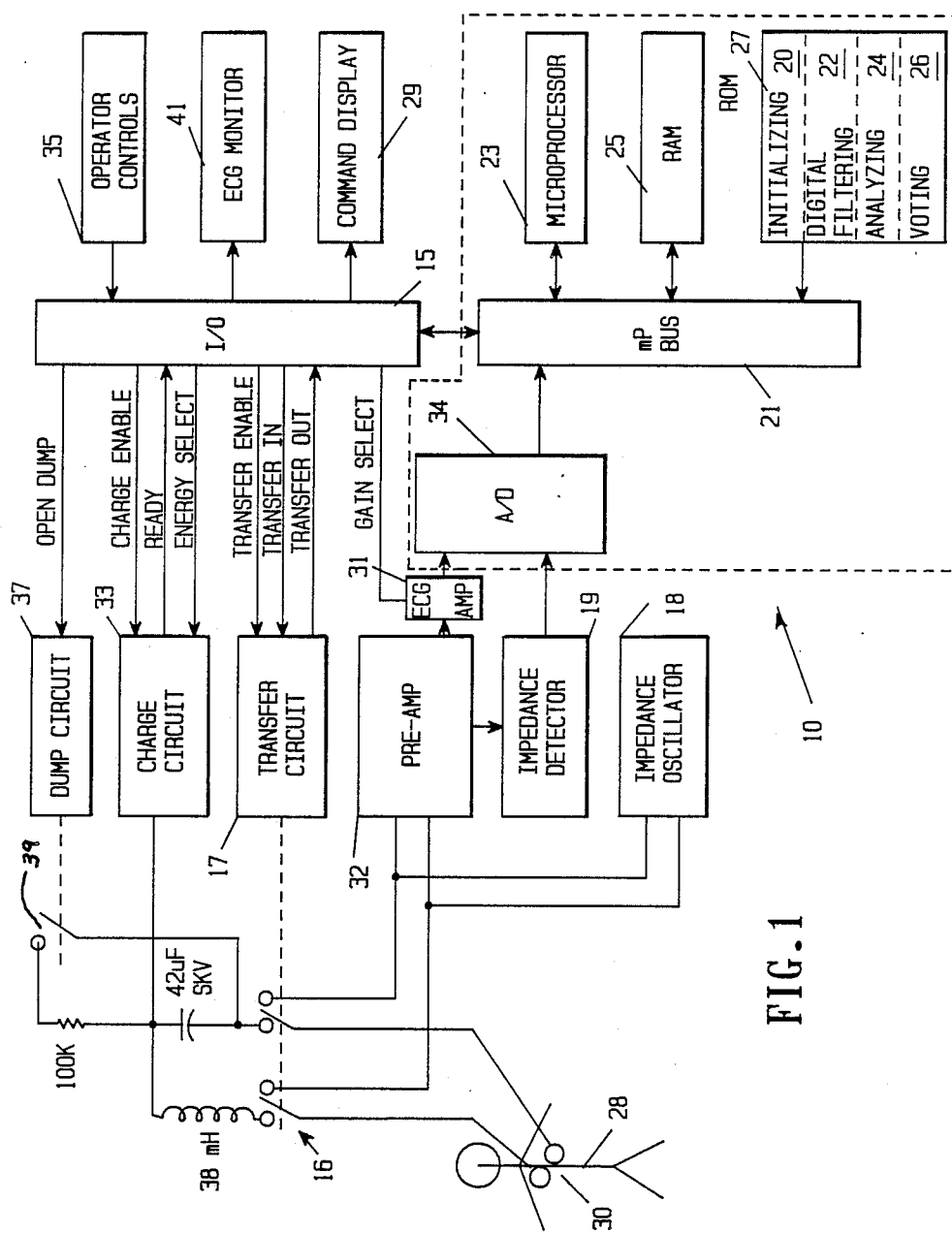
FIG. 1 is a block diagram of a defibrillator that includes an ECG interpreter.

The ECG interpreter 10, as shown in FIG. 1, is a program which can be executed by a conventional microprocessor contained within a conventional defibrillation system, where the microprocessor operates on digitized samples provided by the system.

The patient 28 is connected to the defibrillator through a pair of conventional defibrillation electrodes 30. The electrodes can be disposable. The signals from the electrodes pass through a double pole-double throw relay 16 which is activated by the transfer circuit 17 of the defibrillation system. Relay 16 has two positions: an analysis position and a transfer position. When the relay 16 is in the analysis position, the interpreter 10 receives and processes the signals produced by electrodes 30. For the relay 16 to be in the transfer position, the interpreter 10 must have interpreted the signals produced by electrodes 30, decided that they represent a condition requiring treatment, and administered a shock to the patient. In a semiautomatic mode, the relay 16 would not be switched to the transfer position until a switch is manually activated.

The relay in FIG. 1 is shown in the analysis position, which connects electrodes 30 to conventional preamplifier 32 and a conventional impedance oscillator 18. Impedance oscillator 18 produces a sinusoidal current waveform at approximately 32 kHz. This current passes through patient 28, giving rise to a voltage dependent upon the impedance of patient 28. This voltage and the ECG voltage are received by preamplifier 32. One output from the preamplifier 32 is connected to the ECG amplifier 31. The combined gain of the preamplifier 32 and ECG amplifier 31 is selectable in the range of 200 to 3200. This gain is nominally selected to be 1000.

The other output from preamplifier 32 is sent to a conventional impedance detector 19, which receives the 32 kHz sinusoidal voltage and produces a direct current signal whose magnitude is proportional to the impedance of patient 28. The ECG and impedance detector signals are received by a conventional analog-to-digital (A/D) converter 34 which produces an 8-bit digital signal in response to its inputs. The output of A/D converter 34 is received by microprocessor bus 21, which, in turn, provides signals to microprocessor 23 and random access memory (RAM) 25. The read-only memory (ROM) 27 contains the program that controls the operation of the microprocessor 23. Microprocessor 23 can, for example, be a 8/16-bit hybrid microprocessor, such as an Intel 80C88, while the RAM 25 and ROM 27 can be 6264 and 27C64 chips, respectively. The microprocessor 23 uses the impedance data derived from the impedance detector 19 to determine whether the impedance between the electrodes 30 is in, a range of impedances that is characteristic of the impedance between a pair of properly applied and connected defibrillation electrodes. This impedance range is approximately 30 to 200 ohms. An impedance below this acceptable range may be indicative of a short circuit. An impedance above this acceptable range may be indicative of either an open circuit or incorrect electrodes (e.g., monitoring electrodes) connected to the preamplifier 32.

After making its impedance determination, microprocessor 23 sends signals to input/output (I/O) bus 15. If the microprocessor 23 determines that the electrodes either are not properly connected to a patient or are of the wrong type, it causes a message to this effect to be displayed on command display 29. Otherwise, microprocessor 23 begins to collect the ECG data produced by electrodes 30 through preamp 32, ECG amp 31, A/D converter 34, and microprocessor bus 21. These 8-bit samples are taken every 10 milliseconds over a three-second period. The data collected over the three-second period then comprises 300 samples. These samples, which are digitized to 8 bits, are stored in RAM 25 under control of microprocessor 23.

In a manner to be described in detail subsequently, microprocessor 23 next proceeds to analyze the data stored in RAM 25 under control of a program stored in ROM 27. The program constitutes four components. An INITIALIZING function 20 (whose block diagram is shown in FIG. 4) is executed at system start-up to initialize the data structures stored in RAM 25 that are used by ECG interpreter 10. The three remaining functions—DIGITAL FILTERING 22, ANALYZING 24, and VOTING 26—are executed every three seconds.

The DIGITAL FILTERING function 22 processes a sequence of digitized ECG data stored in RAM 25 to both update internal, software-based digital filters and derive specific variables required by the ANALYZING function 24. The ANALYZING function 24 derives additional variables to test for the presence of noise, asystole, and no-treat conditions. The result of this testing is tallied for the current period.

The VOTING function 26, which can be performed in two modes, next polls the current result and the results of prior periods to specify whether the system output should be characterized as a noise, treat, or no-treat condition. In a monitoring mode, the interpreter can indicate that the patient's condition is suitable for treatment (e.g., on a 3 out of 4 vote). In a treating mode, the interpreter can enable a defibrillator to treat the patient when appropriate conditions are met (e.g., on a 2 out of 3 vote).

In a semiautomatic defibrillation system, after the interpreter (operating in a treating mode) has indicated that a treat condition exists, the operator responds by deciding whether to manually treat the patient. In an automatic defibrillation system, the microprocessor uses the system output produced by VOTING function 26

(in the treating mode) to cause the defibrillator shown in FIG. 1 to administer an appropriate shock to patient 28.

Once at least one treat period has been detected for the patient, microprocessor 23 causes a CHARGE ENABLE signal to be sent from I/O bus 15 to charge circuit 33 and an OPEN DUMP signal to be sent to the dump circuit 37. Microprocessor 23 also causes an ENERGY SELECT signal to be transferred from I/O bus 15 to charge circuit 33. Charge circuit 33 causes the 42 microfarad, 5 kilovolt capacitor to be charged with the selected energy. If the decision to treat has been made and the charge circuit is ready as indicated by the READY signal, microprocessor 23 causes a TRANSFER ENABLE signal to be sent from I/O bus 15 to transfer circuit 17. In the case of a semiautomatic defibrillator, the decision to treat requires input by an operator through operator controls 35. The operator thereby causes the defibrillator to enter the ANALYZING function and can select the amount of energy to be administered to the patient.

The TRANSFER ENABLE signal is followed by a TRANSFER IN signal which causes transfer circuit 17 to switch relay 16 to the transfer position. This connects a series circuit comprising the 42 microfarad capacitor and a 38 mH inductor to electrodes 30 and administers a shock of appropriate energy to patient 28. When transfer circuit 17 causes relay 16 to switch, transfer circuit 17 returns a TRANSFER OUT signal to microprocessor 23 through I/O bus 28 and microprocessor bus 21 signifying that the transfer circuit has activated. The microprocessor 23 also deactivates the OPEN DUMP signal at the time of charge transfer.

If it is decided that the 42 microfarad capacitor should be discharged internally, the I/O bus 15 deactivates an OPEN DUMP signal to dump circuit 37, deactivating relay 39 and discharging the 42 microfarad capacitor through a 100 K ohm resistor. The decision to discharge internally will be made, for example, if the time to defibrillate exceeds a predetermined limit.

As ECG signals are received by the microprocessor bus 21 from A/D converter 34, microprocessor 23 causes these signals to be transmitted through microprocessor bus 21 and I/O bus 15, to ECG monitor 41. Additionally, I/O bus 15 can be connected to a voice synthesizer and/or a beeper (not shown) to provide audible signals to users of the defibrillation system.

Details of each of the four functions performed in accordance with software stored in ROM 27 will be discussed in the remainder of this detailed description.

INITIALIZING FUNCTION

Figure 2:
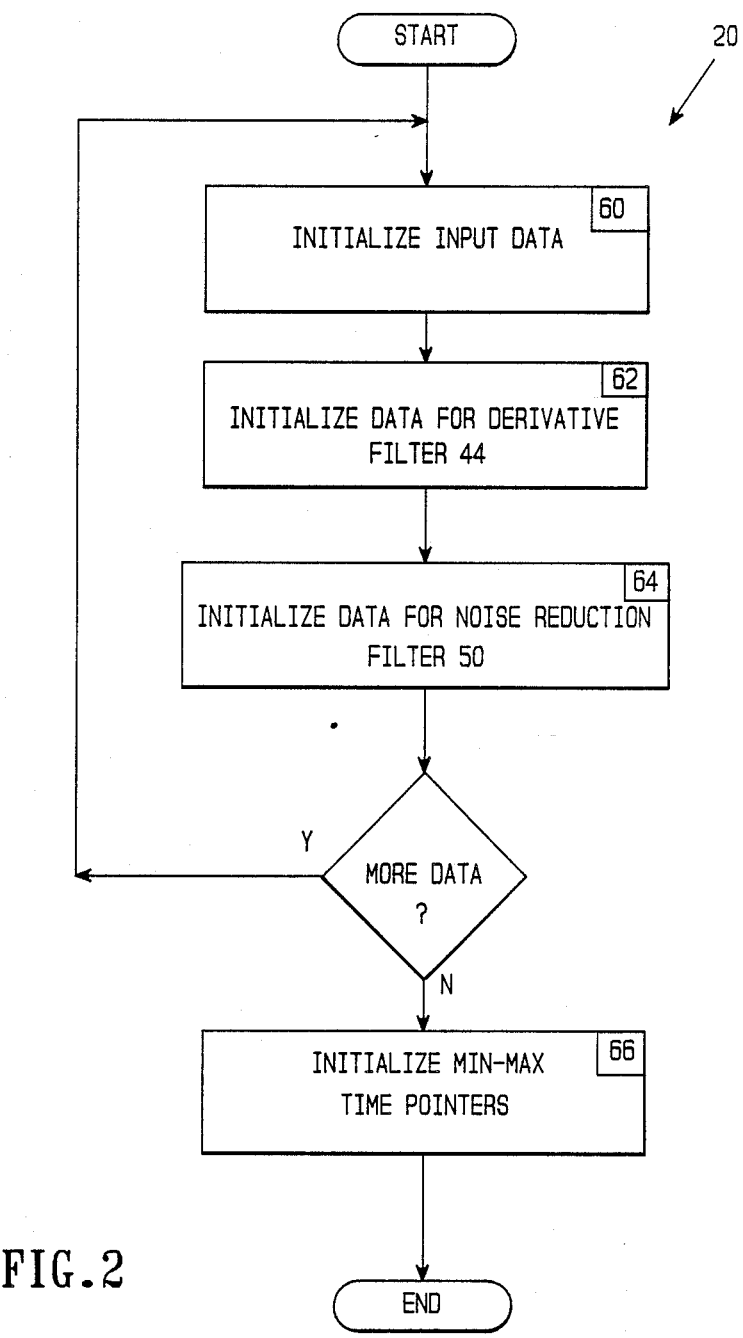
FIG. 2 is a flow chart of the INITIALIZING function.

As shown in the INITIALIZING function flow chart of FIG. 2, at system start-up, specific data structures and data items are initialized. At step 60, a storage buffer for sequences of ECG samples is initialized. In one embodiment, the storage buffer holds more than 300 ECG samples. In steps 62 and 64, data values prior to the start-up time are initialized for the derivative filter 44 and noise reduction filter 50, to be described subsequently (see FIG. 4). In step 66, the times associated with the initial minimum and maximum values in the current sequence of ECG samples are made equal to the time when the sampling is started.

DIGITAL FILTERING FUNCTION

Figure 3A:
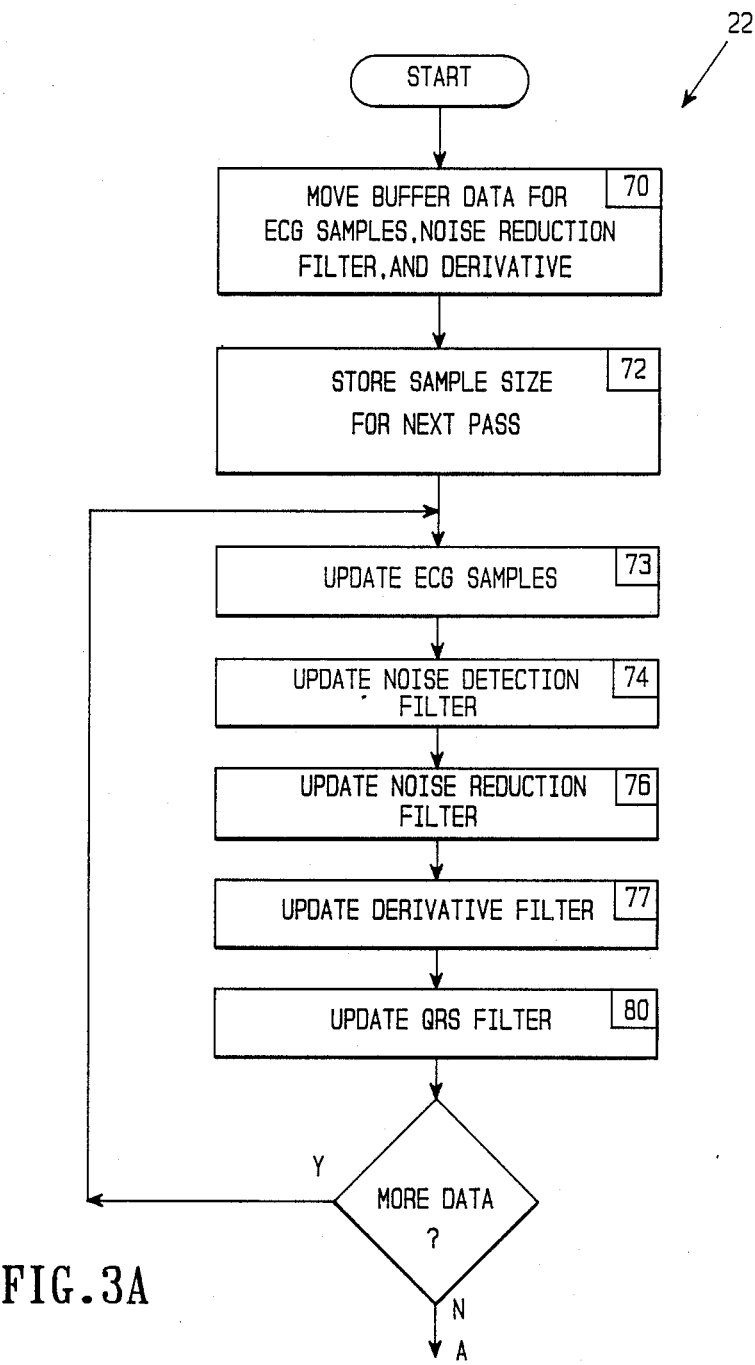
FIGS. 3A and 3B are a flow chart of the processing performed by the DIGITAL FILTERING function.
Figure 3B:
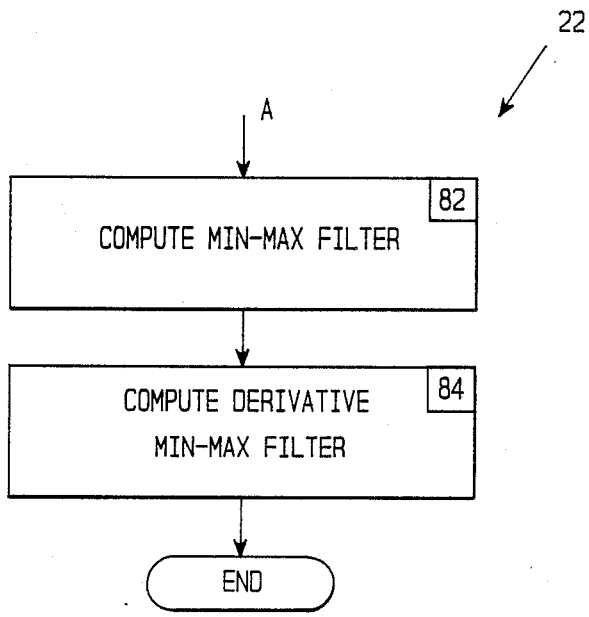

For each three-second sequence of ECG data, the DIGITAL FILTERING function is executed in accordance with the steps shown in the flow chart of FIGS. 3A and 3B. The DIGITAL FILTERING function processes the ECG data in order to update the digital filters and derive variables required for later functions.

In step 70, the last several ECG samples from the prior iteration are moved to the beginnings of the working buffers for the ECG sample storage and the noise reduction filter 36, derivative filter 44, and noise detection filter 50. In step 72, the number of ECG samples, normally 300, is stored in RAM 25. In step 73, this three-second sequence of ECG samples is moved from the input buffer to the ECG samples working buffer. The input buffer is loaded with an ECG sample every 0.01 second from A/D converter 34.

Figure 4A:
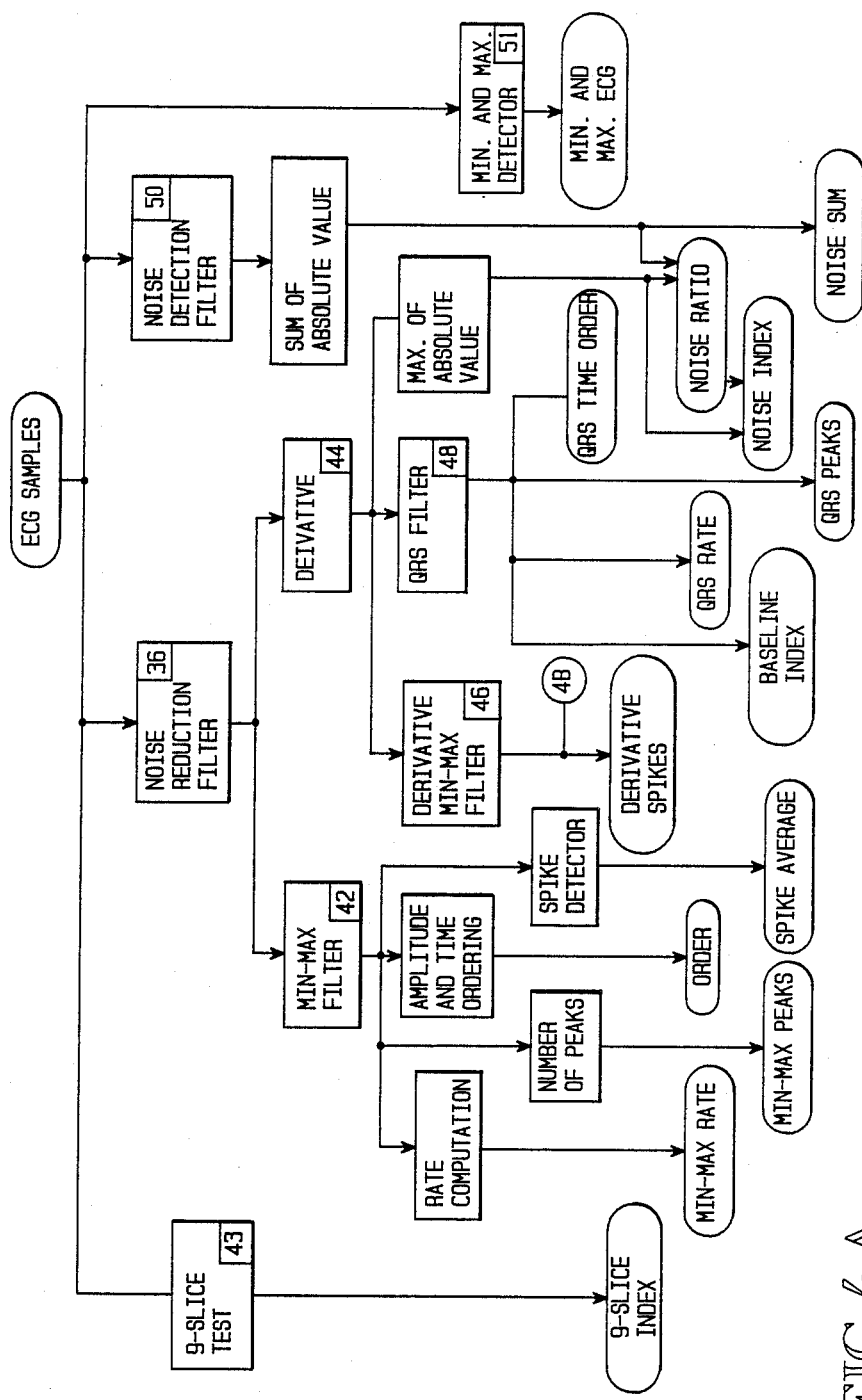
FIGS. 4A and 4B are a block diagram of the data flow required for processing the ECG samples.
Figure 4B:
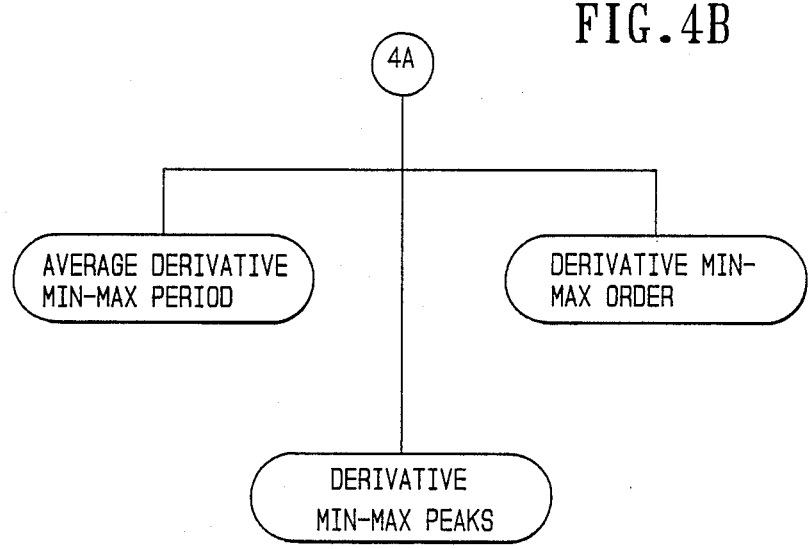

Turning to FIGS. 4A and 4B, a tree diagram illustrates the data flow of the ECG samples, as well as the resulting filter outputs, through the ECG interpreter 10. The ECG samples are direct inputs to software-based 9-slice test 43, digital noise reduction filter 36, noise detection filter 50, and minimum-maximum detector 51. The results produced by the 9-slice, test 43 are used to produce an index. The 9-slice index is one factor which aids in detecting the existence of a possible treat condition.

In a second branch of the data flow tree diagram, the noise reduced ECG samples output from noise reduction filter 36 are input to software-based minima-maxima filter 42 and a derivative filter 44. The sequence of minima and maxima output from the minima-maxima filter 42 are processed to calculate a rate of occurrence, the number of peaks, the presence of a time and amplitude pattern (order), and an index of narrow transitions ("spikes") in the output of minima-maxima filter 42. The sequence of derivatives output by derivative filter 44 are input to a derivative minima-maxima filter 46. They determine, as shown in FIG. 4B, (a) the number of spikes in the derivative of the ECG samples, (b) derivative min-max peaks (the number of minima and maxima in three seconds of the output of filter 44), (c) derivative min-max order (the minimum of the maximum time between two consecutive maxima (minima) minus the minimum time between two consecutive minima (maxima) of the output of filter 44), and (d) average derivative min-max period (the average of maximum and minimum time used in the derivative min-max order calculation). The sequence of derivatives is also input to a QRS filter 48 to determine a baseline index, a QRS rate, the number of QRS peaks, and a QRS time order. Additionally, the maximum of the absolute value of the output of derivative filter 44 is calculated to determine a noise ratio and a noise index.

In a third branch of the data flow tree diagram, the ECG samples are input to a software-based noise detection filter 50. The absolute value of the noise samples output from the noise detection filter 50 is summed to derive a noise sum and a noise ratio.

In a fourth data flow branch, the minimum and maximum ECG sample values are identified in detector 51. The values calculated from the ECG samples are subsequently used in testing for noise and in the calculation of the 9-slice index. A more detailed description of each function is presented below.

Returning to FIG. 3A, in repetitions of step 74, each ECG sample is processed through noise detection filter 50 to derive a sequence of noise values. The noise detection filter uses the following transformation:

$$N_t = U_t - 3U_{t-1} + 4U_{t-2} - 3U_{t-3} + U_{t-4}$$

where $N_t$ is the noise value output for time t and $U_t$ is the ECG sample for time t.

In repetitions of step 76 (see FIG. 3A), for each new sample in the sequence of ECG data, noise reduction filtering is executed to derive a sequence of noise-reduced ECG values. The processing for noise reduction filter 36 transforms the input using the following equation:

$$R_t = U_t + 1.618(U_{t-1} - U_{t-3}) - U_{t-4} + (15/16)R_{t-1}$$

where $R_t$ is the noise-reduced ECG value for time t.

By repetitions of step 78, the sequence of noise reduced ECG samples is processed by derivative filter 44 to produce the derivative of the function defined by the sequence of noise-reduced samples. The derivative at each sample time is defined using the formula:

$$D_t = R_t + R_{t-1} - R_{t-3} - R_{t-4}.$$

where $D_t$ is the derivative filter output for time t and $R_t$ is the noise-reduced ECG value for time t. The derivative filter 44 is chosen in part to pass signals in a frequency band that includes most of the signal energy of ECGs.

In repetitions of step 80, the sequence of derivatives is then processed by digital QRS filter 48. The QRS filter derives a moving window average of the absolute value of the derivative filter output. This operation tends to show QRS peaks. The transformation used for the QRS filter is shown below:

$$Q_t = |D_t| + |D_{t-1}| + |D_{t-2}| + |D_{t-3}| + |D_{t-4}| + |D_{t-5}| + |D_{t-6}| + |D_{t-7}|.$$

where $Q_t$ is the QRS filter output for time t and $D_t$ is the derivative filter output for time t.

After the noise reduction filter, noise detection filter, derivative filter, and QRS filter have been updated for each sample, the sequence of ECG samples is processed through a digital minima-maxima filter 42 (step 82 in FIG. 3B) and a digital derivative minima-maxima filter (step 84).

Figure 5:
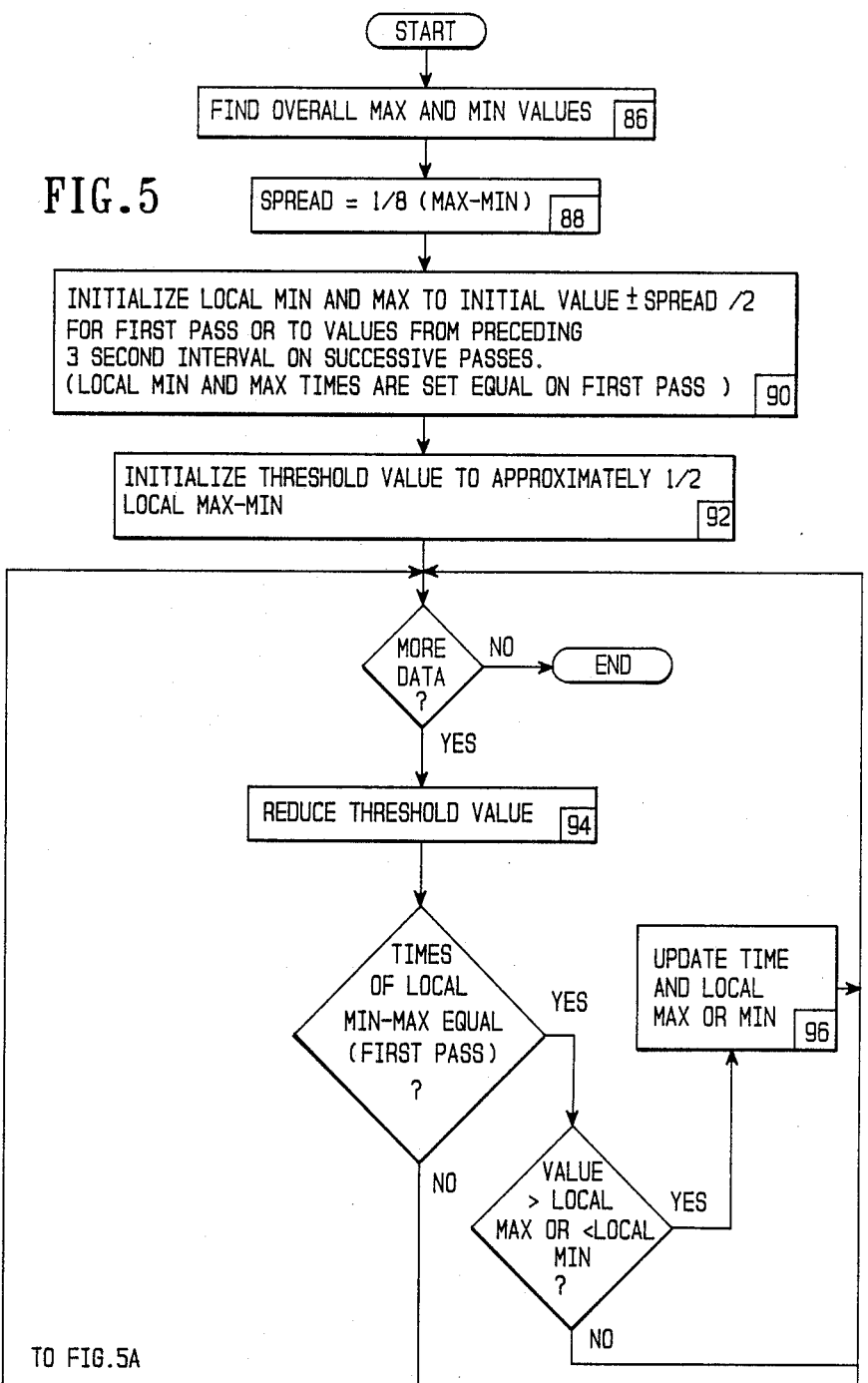
FIGS. 5 and 5A are a flow chart of the processing performed by the minima-maxima digital filter.
Figure 5A:
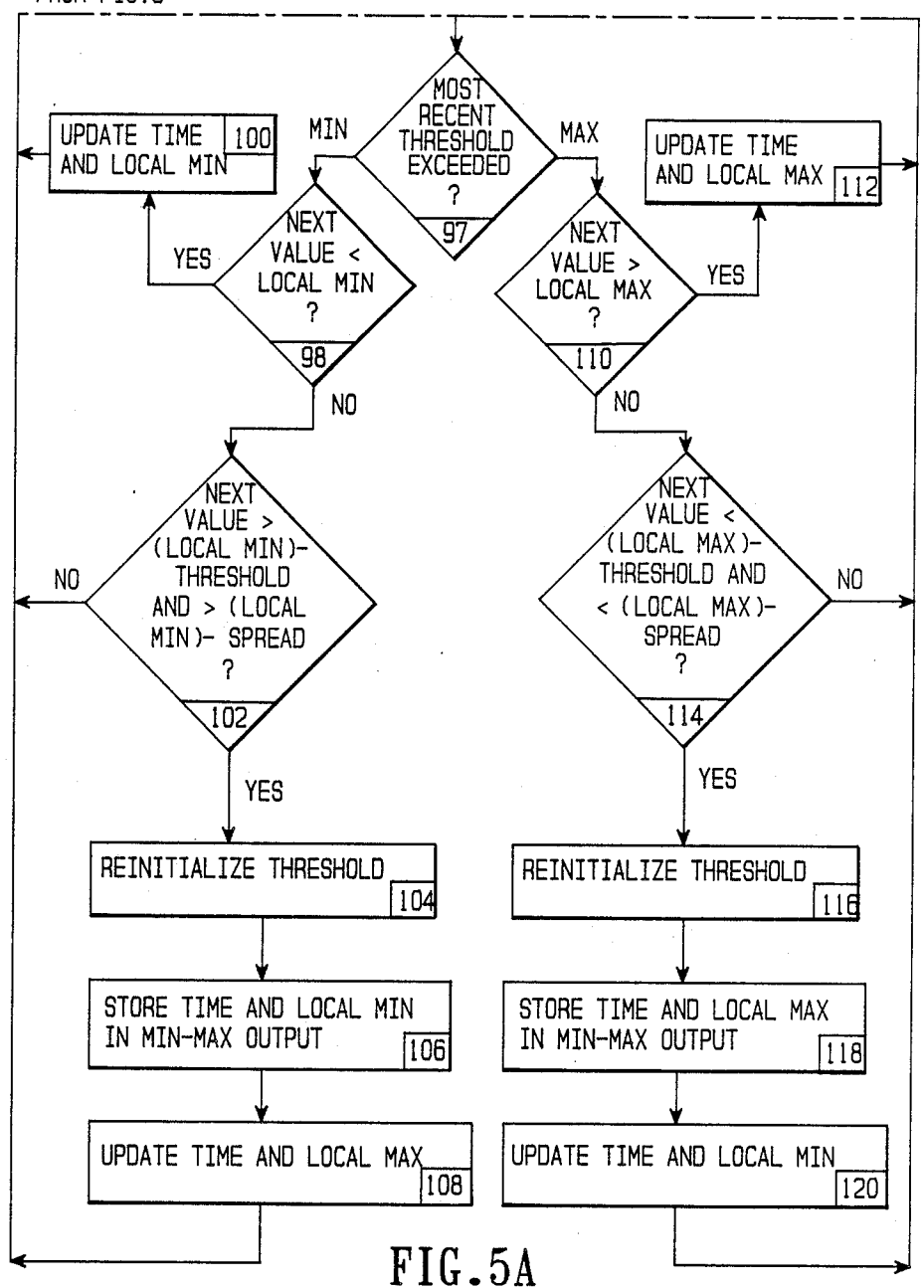
Figure 6:
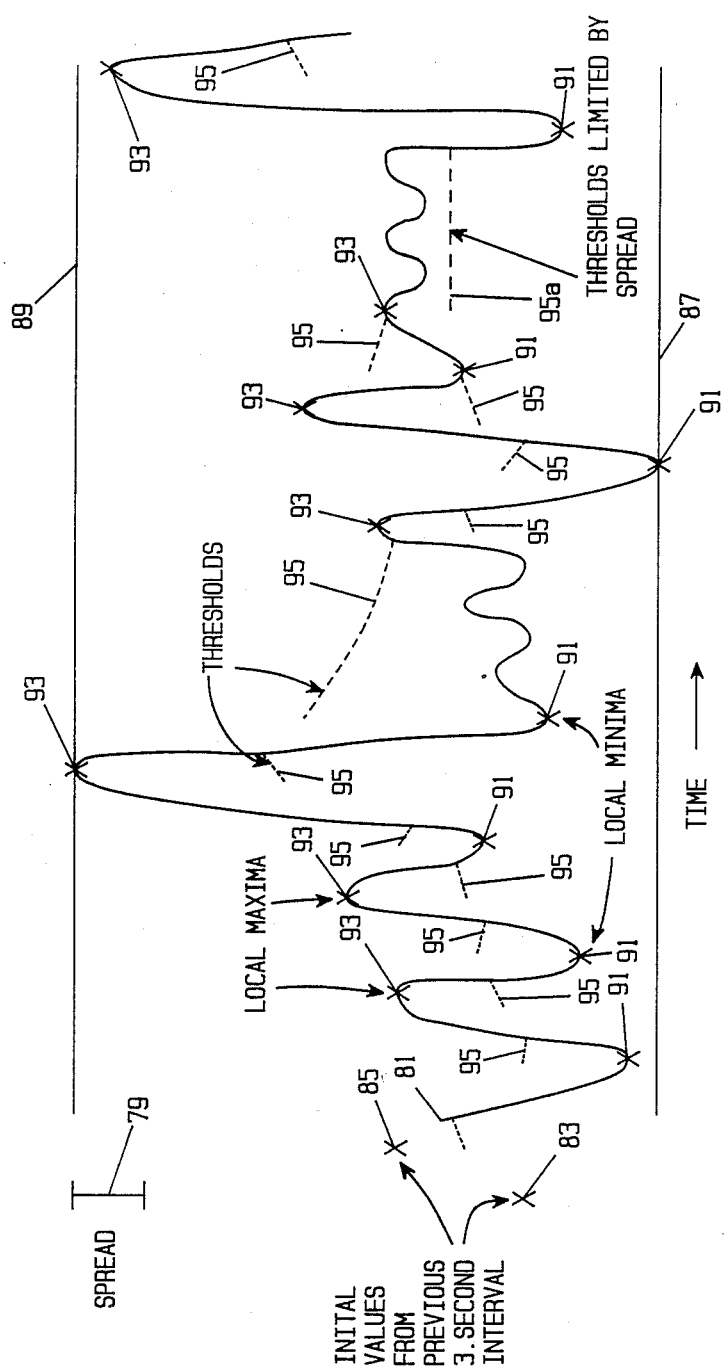
FIG. 6 is an example of the processing performed by the minima-maxima filter on a sequence of ECG samples.

A flow chart of the processing performed by the minima-maxima filter 42 is shown in FIG. 5. Filter 42 detects the significant local extrema in the ECG waveform by defining a series of changing thresholds and picking peaks in the waveform when the waveform crosses a threshold. An example of the processing performed by the minima-maxima filter 42 on a sequence of ECG samples is shown in FIG. 6.

Minima-maxima filter 42 produces a sequence of pairs of values. A pair of values is produced each time the filter detects either a local minimum 91 or a local maximum 93 (see FIG. 6). One of the values is the amplitude of the local minimum or local maximum, and the other is the time of occurrence of this local extremum. The sequence of ECG samples is first examined to identify the overall minimum and maximum values (87 and 89, respectively) (step 86) in the entire sequence of 300 ECG samples. The spread 79 is then defined as one-eighth of the difference between the minimum and maximum values 87 and 89 (step 88). Unless the filter is receiving its first sequence of ECG samples, an initial local minimum 83 and local maximum 85 are carried over from prior local minimum and local maximum values and used as references in comparison (step 90). If the filter is receiving its first sequence of values, the local minimum and maximum are set equal to the value of the initial ECG sample 81, minus or plus one-half of the spread, respectively. The filter will ignore all consecutive maximum-minimum differences that are less than the spread in order to avoid responding to insignificant fluctuations in the ECG samples.

To find new local minimum and local maximum values, a threshold value (see 95 in FIG. 6) is defined (step 92). With each new sequence of ECG samples, the threshold value 95 is initially defined as approximately one-half of the difference between the most recent local maximum and local minimum. The filter then does a sequence of comparisons for each ECG sample to identify maximum and minimum values. Each time an ECG sample is compared for local minimum or maximum and no new local minimum or maximum value is detected, the threshold value 95 is changed by a smaller fraction of the difference between the last previously determined local extremum and the last local extremum. Thus, the threshold value 95 slowly converges toward the value of the last local extremum, as shown in FIG. 6. In some embodiments, the threshold value 95 can be prevented from approaching the value of the last local extremum by less than the spread, as shown by curve 95a in FIG. 6. By using this approach, only the major features of the ECG sample sequence will be analyzed as local extrema (step 94).

At system start-up, the first ECG sample is compared to determine if it is greater than the local maximum 85 or less than the local minimum 83. If either condition is met, the time and value of this local maximum or local minimum is updated to replace the reference local maximum and local minimum (step 96). If neither condition is met, ECG samples are compared in subsequent passes until one is found to be greater than the local maximum 85 or less than the local minimum 83. During subsequent passes, the most recent threshold value curve 95 to be crossed is tested (step 97) to determine whether it was an upwardly converging (minimum) or downwardly converging (maximum) threshold value. One branch of processing is executed when a minimum threshold is crossed and the other branch is executed when a maximum threshold is crossed. When the branch for a minimum threshold is executed, the next filter input value is compared to the local minimum 91 (step 98). If it is less than the local minimum 91, the current time and value replace the local minimum time and value as the reference (step 100). If the next value is not less than the local minimum 91, then this next value is tested to determine if it is both greater than the local minimum 91 plus the threshold value 95 and greater than the local minimum 91 plus the spread 79 (step 102). If it is, the threshold value 95 is reinitialized to approximately one-half of the separation between the last local maximum and the local minimum (step 104) and the time and local minimum are stored as outputs of the minima-maxima filter 42 (step 106). The time and value of the local maximum are then updated (step 108). Upon the subsequent execution of step 97, the other branch (for a maximum threshold) will be executed.

When the branch for a maximum threshold is executed, the current value is compared to a local maximum (step 110), and if it is greater than the local maximum 93, the time and value for the local maximum replace the current time and value as the reference (step 112). If not, the current value is tested to determine if it is both less than the local maximum 93 minus the threshold value 95 and less than the local maximum 93 minus the spread 79 (step 114). If it is, the threshold value 95 is reinitialized (step 116) and the time and value of the local maximum are stored as outputs of the minima-maxima filter 42 (step 18). Additionally, the time and value of the local minimum are updated (step 120). Upon the subsequent execution of step 97, the other branch (for a minimum threshold) is executed.

Figure 7A:
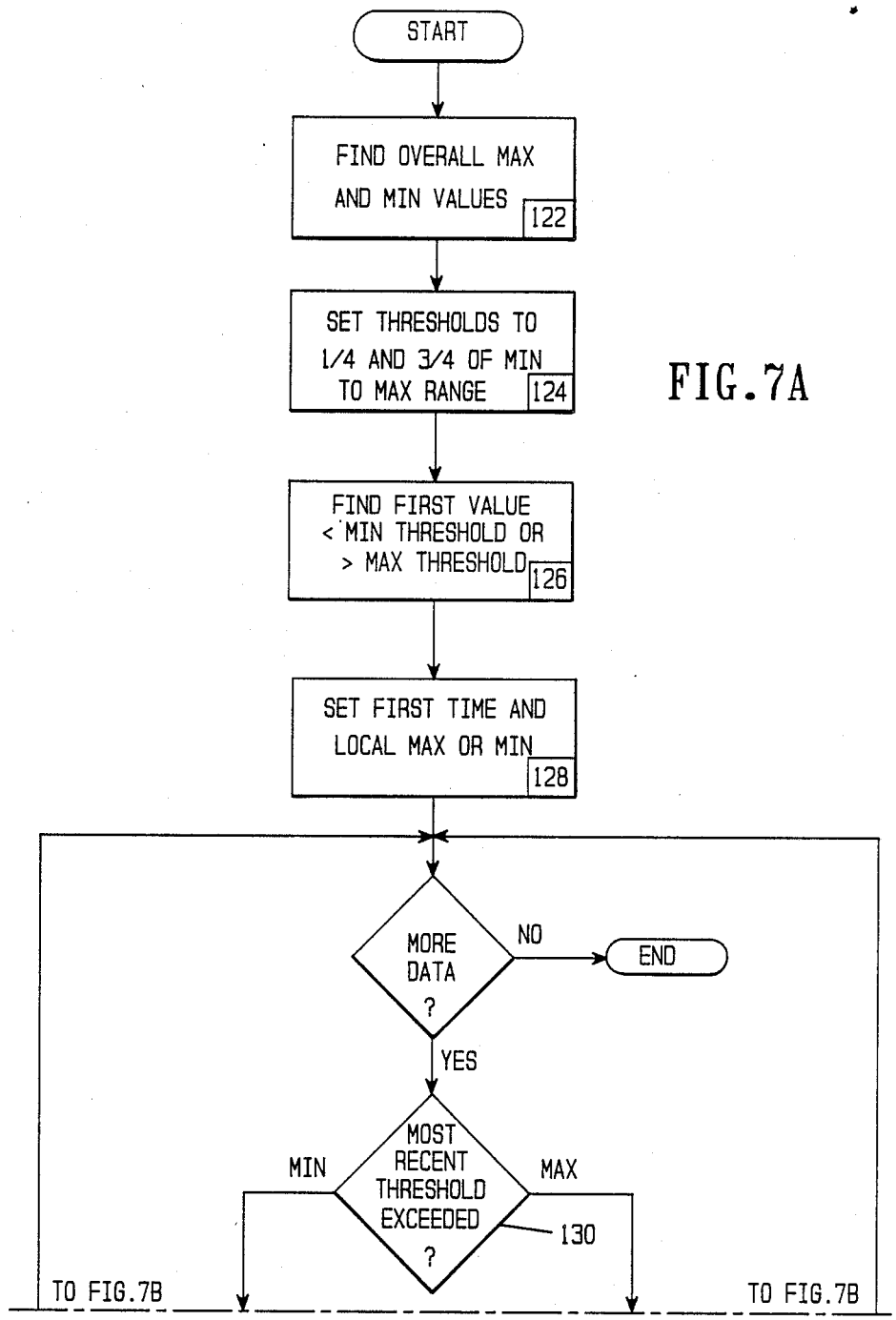
FIGS. 7A and 7B are a flow chart of the processing performed by the derivative minima-maxima digital filter.
Figure 7B:
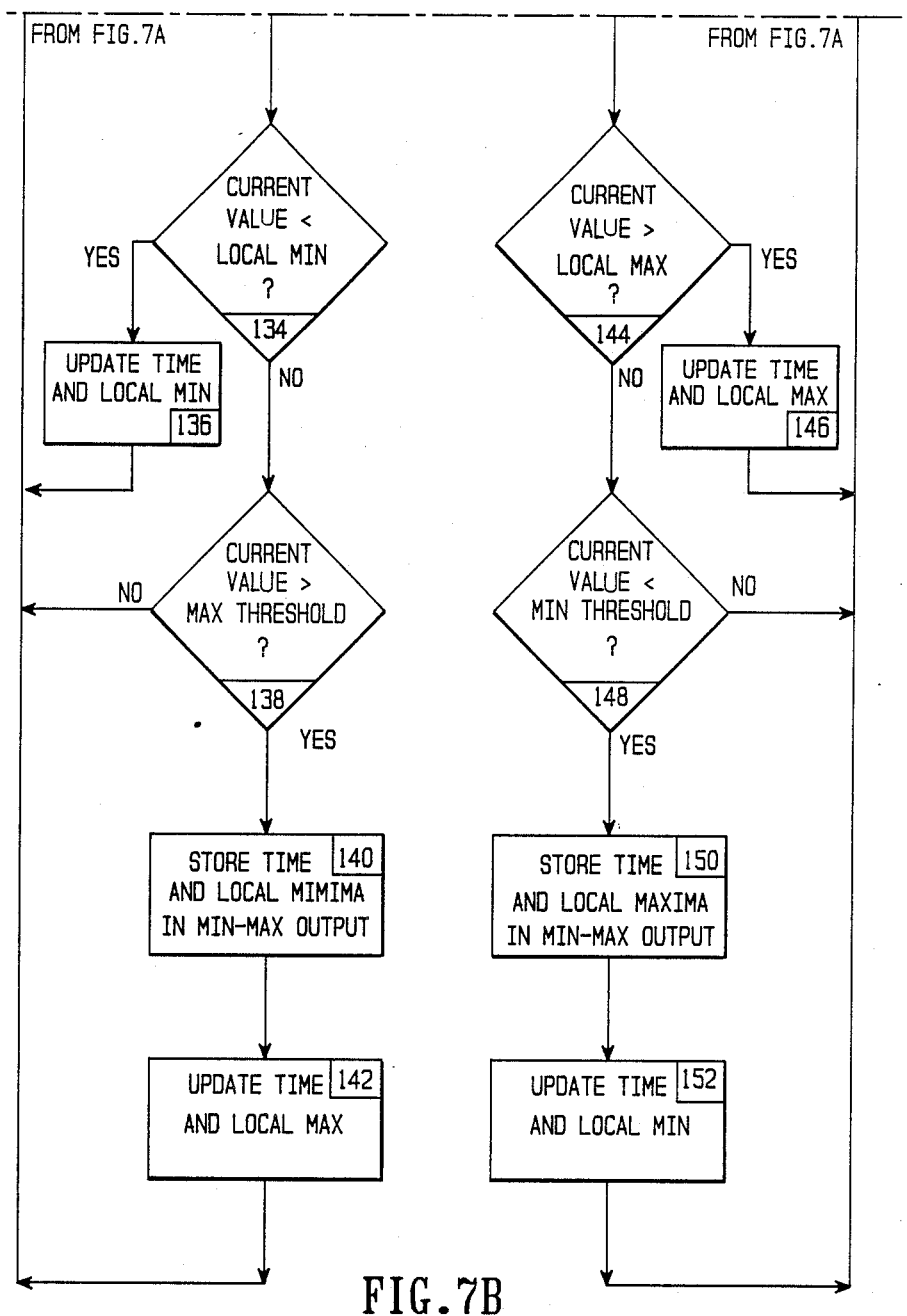

Referring to FIGS. 4 and 3B, the sequence of derivative filter outputs is processed by a digital derivative minima-maxima filter 46 in step 84 of the DIGITAL FILTERING function. Filter 46 identifies local extreme values in the waveform that is the first derivative of the ECG waveform. The first derivative waveform is determined by derivative filter 44. A flow chart of the processing performed by the derivative minima-maxima filter 46 is shown in FIG. 7. An example of the processing performed by the derivative minima-maxima filter in a sequence of ECG samples is shown in FIG. 8.

Figure 8:
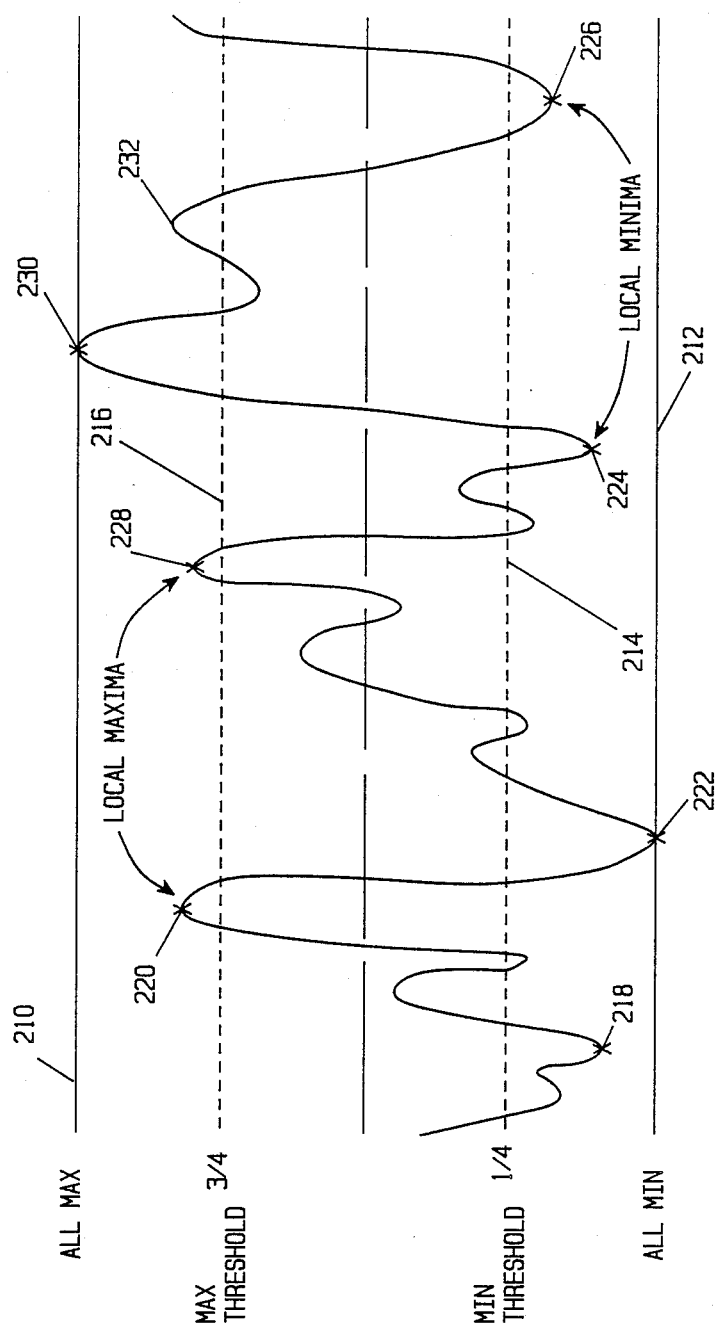
FIG. 8 is an example of the processing performed by the derivative minima-maxima filter on a sequence of ECG samples.

Referring to FIGS. 7 and 8, the entire sequence of derivative samples is initially processed to identify the overall maximum and minimum sample values, 210 and 212, respectively (step 122). A minimum threshold 214 is then set at the overall minimum plus one-fourth the difference between the overall minimum and maximum values. A maximum threshold 216 is set at the overall minimum value plus three-fourths of the difference between the overall maximum and minimum values (step 124).

Before entering the interations to determine the local minima and maxima, it is necessary to establish initial values for the local minima and local maxima, 218 and 220, respectively. To do this, each derivative sample is tested in sequence to identify the first sample that is less than the minimum threshold 214 or greater than the maximum threshold 216 (step 126). When identified, the time and value are stored as the local maximum or local minimum (step 128). With the initial local minimum and maximum established, the entire sequence of derivative samples is then processed to identify the filter outputs. Since local minima (218, 222, 224, and 226) and maxima (220, 228, 230, and 232) must lie outside the minimum and maximum thresholds, 214 and 216, respectively, at step 130, the threshold is tested to determine if the minimum or maximum threshold was the most recent threshold exceeded. One branch of processing is executed if the minimum threshold is the most recently exceeded and a separate branch is executed if the maximum threshold is the most recently exceeded.

When the branch for a minimum threshold is executed, the next filter input value is compared to the local minimum (step 134). If less than the local minimum, the time and value of the current sample replace the local minimum as the reference (step 136). If not, the current value, is tested to see if it is greater than the maximum threshold (step 138). If greater than the maximum threshold, the time and value of the local minimum are stored as a filter output (step 140). The time and local maximum are then updated (step 142). If not greater than the maximum threshold (step 134), this branch is executed again. Upon the subsequent execution of step 130, the branch for exceeding a maximum threshold will be executed.

When the most recent threshold to be crossed is the maximum threshold, the current value is compared to the local maximum (step 144). If the current value is greater, the time and value of the current value replace the time and value of the local maximum as the new reference (step 146). If not, the current value is tested to determine if it is less than the minimum threshold (step 148). If less, the time and value of the local maximum are stored as output of the filter (step 150). The time and value of the local minimums are then updated (step 152). Upon the subsequent execution of step 130, the branch for crossing a minimum threshold will be executed. If not less than the minimum threshold (step 148), this branch is executed again.

Figure 9:
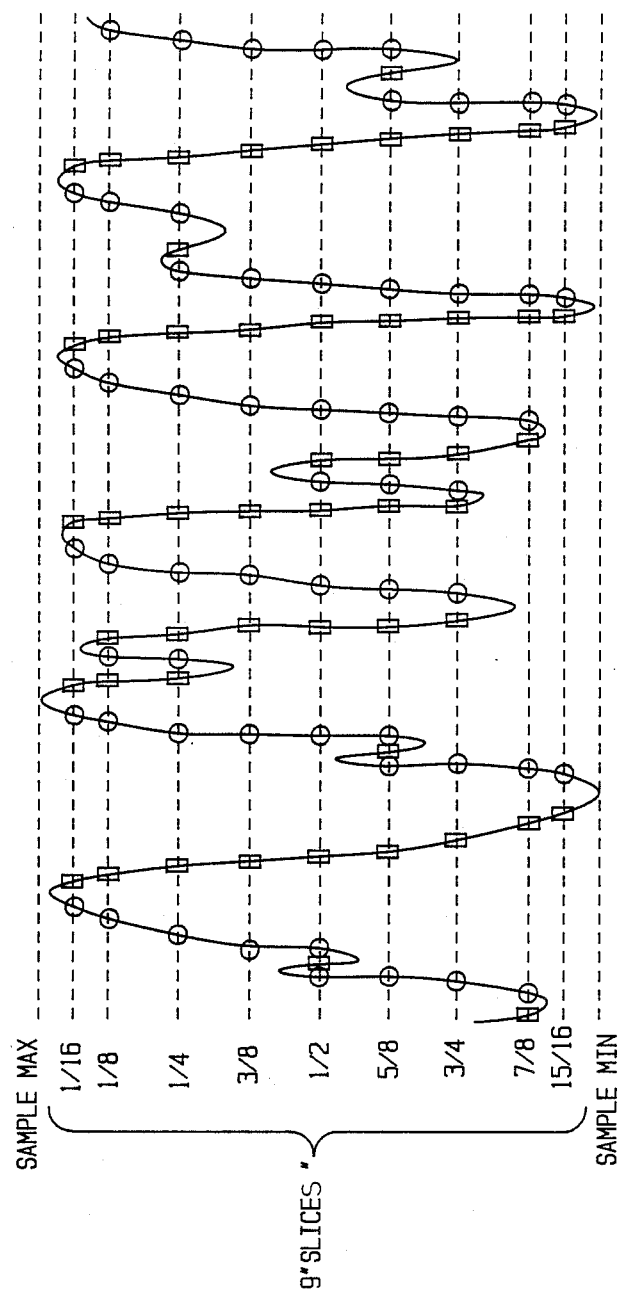
FIG. 9 is an example of the processing performed by the 9-slice test.

The 9-slice test (reference numeral 43 in FIG. 4A) can be explained with reference to FIG. 9. FIG. 9 represents three seconds of a noisy ventricular tachycardia ECG with a rate below 180 beats per minute (bpm). The rhythm should not be treated. The 9-slice test first calculates the minimum and maximum values attained by the ECG within the segment of data being tested. Next nine levels are defined within the segment of data. The levels are determined by the following fractions of the difference between the minimum and maximum values just determined: 1/16, ⅛, ¼, ⅜, ½, ⅝, ¾, 7/8, and 15/16. For each level, the times of all positive- and negative-going crossings are identified. The maximum and minimum time intervals (measured in sample times) for consecutive positive- and negative-going crossings are computed, resulting in two maximum-minimum pairs for each level. The pairs from levels which are not crossed at least four times within the three second sample are discarded from further consideration. Of the remaining pairs, only those whose sum exceeds 67 sample times (i.e., a heart rate of approximately 180 bpm) are retained.

The index is computed as the minimum of the difference between the maximum and minimum time intervals for each of the retained levels. If there are no pairs satisfying these conditions, the index is set equal to 100.

When applied to the waveform shown in FIG. 9, this test will determine that the "1/16" level has the smallest difference between the maximum and minimum time intervals (i.e., that its crossings are the most nearly periodic).

ANALYZING FUNCTION

After the completion of the DIGITAL FILTERING function, the ANALYZING function is the next to be executed (step 24 in FIG. 1). The microprocessor 23 will analyze at least two consecutive 3-second segments of ECG data. During the ANALYZING function, variables are calculated from the outputs of the DIGITAL FILTERING function and a series of tests are performed on these and other variables to identify asystole, noise, and no-treat conditions. Obviously, the number of data segments can be varied to be any desired predetermined number.

The following detailed description refers to FIGS. 10A-10D.

Asystole: Asystole (i.e., an essentially featureless waveform) is present if either of the two following conditions are met:

1. (Step 160) The maximum of the absolute value of the output of the derivative filter 44 is less than 12 and the number of minima-maxima from the minima maxima filter 42 is less than 12; or 2. (Step 162) The maximum of the absolute value of the derivative filter output is less than 4.

Noise: The following variables are calculated for executing the noise tests:

Noise sum = the sum of absolute values of the noise filter output (step 164);

Noise ratio=Noise sum divided by the maximum of the absolute value of the derivative minima-maxima filter output (step (step 166);

Noise index=(Noise ratio)$^2$ divided by the maximum of the absolute value of the derivative minima-maxima filter 46 (step 168).

The presence of noise is detected if any of the following conditions are met, though other criteria may be used:

1. (Step 169) Noise sum is greater than 800.

2. (Step 170) Number of outputs from the minima-maxima filter 42 are greater than 60.

3. (Step 172) Noise ratio is greater than 25.

4. (Step 174) Noise index is greater than 600 and the maximum of the absolute value of the output of the derivative filter 44 is greater than or equal to 4.

5. (Step 176) The ECG sample has a magnitude of either the upper or lower range limit of A-D converter 34 or within one unit of each limit.

No-Treat:

The following variables are calculated for executing the no-treat tests:

1. Baseline criterion (QRS8) (step 178):

QRS8=the number of QRS filter outputs less than one-eighth the maximum value output from the QRS filter.

Figure 11:
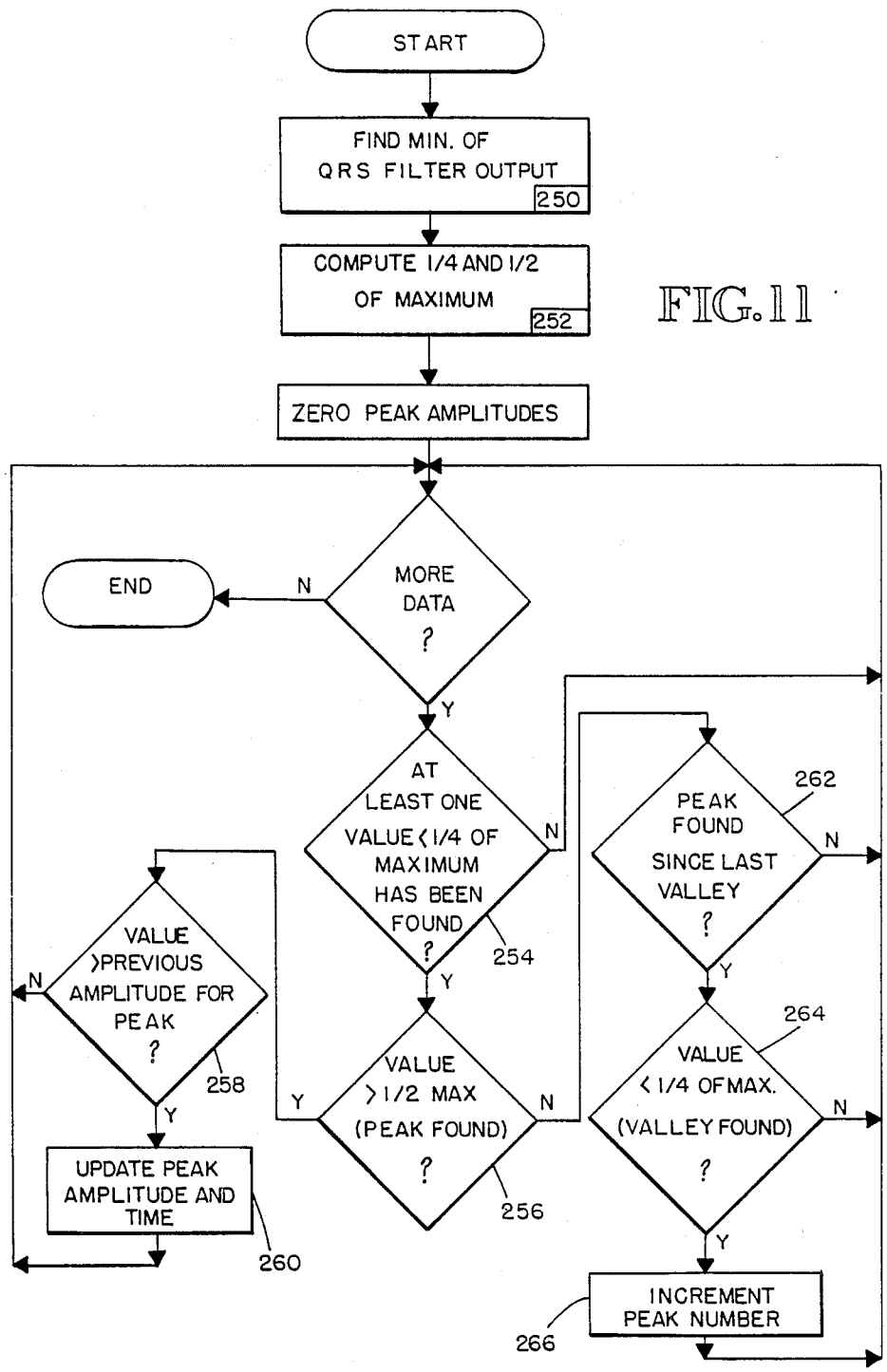
FIG. 11 is a flow chart of the processing performed by the QRS peak detector.

2. Number of peaks in the QRS filter 48 (step 180):

The flow chart for the QRS peak detector is shown in FIG. 11. The maximum of the QRS filter output and the values equal to one-half and one-fourth of the maximum values are identified in steps 250 and 252. Upon entry for each iteration in the QRS peak detector shown in FIG. 11, successive inputs are tested to identify the first input which is less than one-fourth the maximum (step 254). Once found, inputs are tested to determine if the input is greater than one-half the maximum (step 256). If greater than one-half the maximum, the value is checked to see if it is greater than the previous peak amplitude (step 258). If so, the current value and its time of occurrence replaces the prior peak amplitude and time (step 260). If the value is less than one-half the maximum, the value is tested to see if a peak has been found since the last valley (step 262). If so, the current value is tested to see if it is less than one-fourth of the maximum, thereby constituting a valley (step 264). If a valley is found the number of peaks is incremented (step 266).

3. QRS rate (step 182 in FIG. 10B): number of peaks less one divided by the time span between first and last peak detected.

Figure 12:
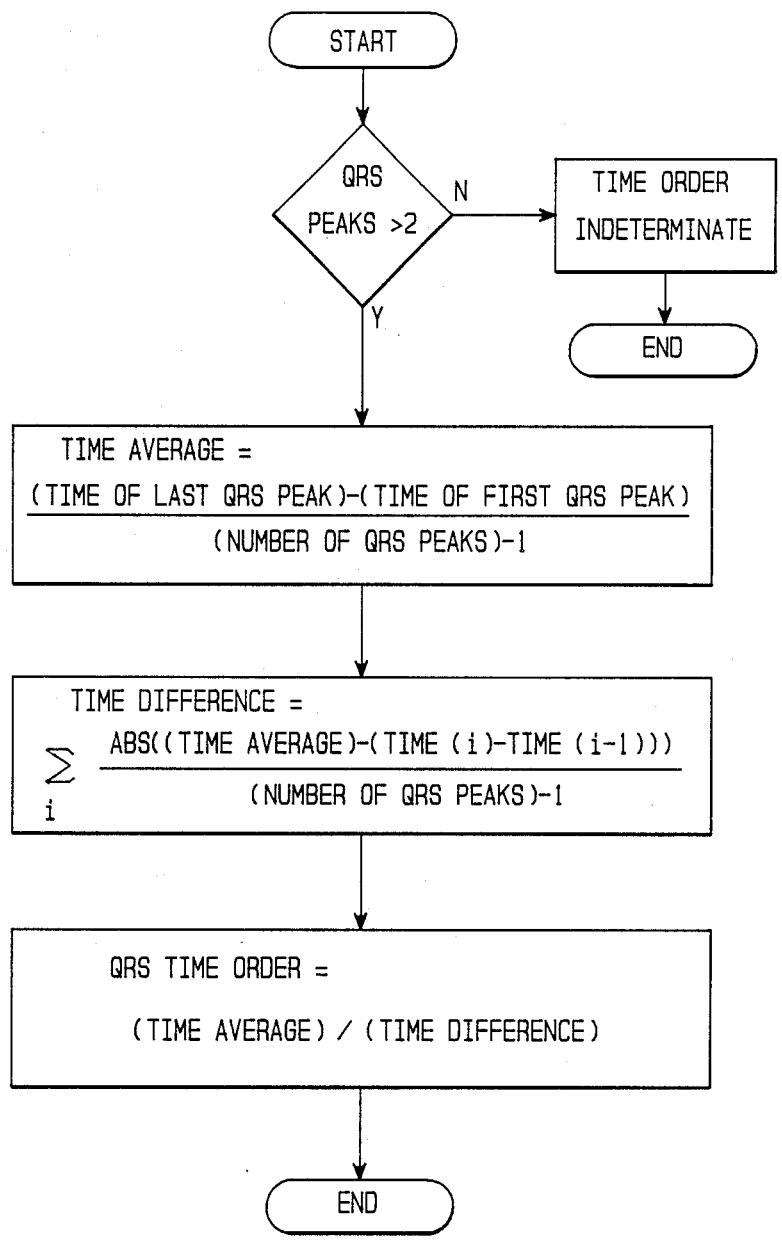
FIG. 12 is a flow chart of the processing performed in the calculation of the QRS time order.

4. QRS Time Order (step 184 in FIG. 10C): A flow chart of the QRS time order calculation is shown in FIG. 12. The QRS time order measures the consistency of the times between QRS peaks. The larger the computed value of QRS time order, the greater the consistency of times between successive QRS peaks.

Figure 13:
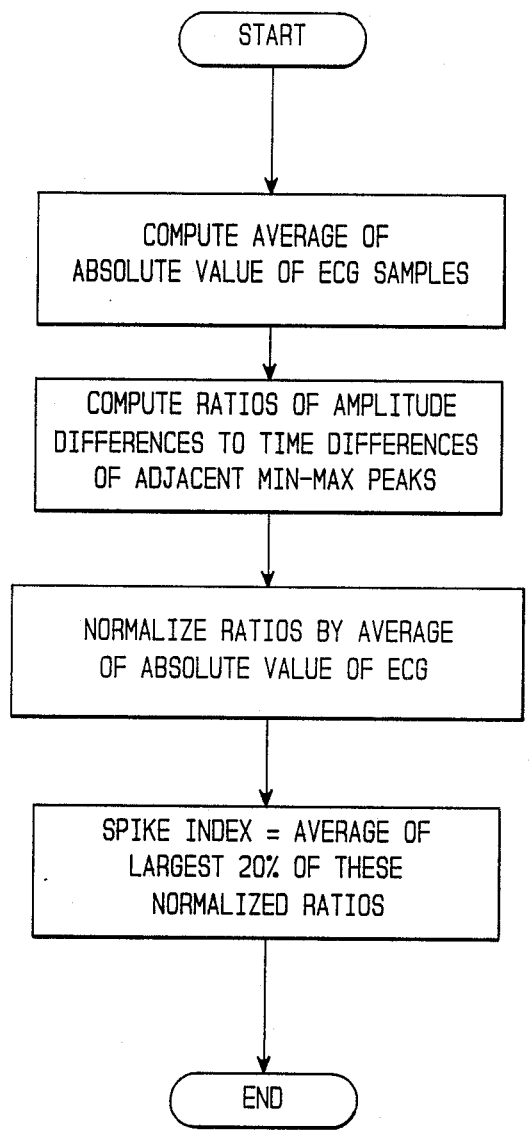
FIG. 13 is a flow chart of the processing performed in the calculation of the spike index.

5. Minima-maxima spike index (step 186 in FIG. 10C): The spike index computation as shown in FIG. 13 produces an index of the narrowest twenty percent of the transitions in the minima-maxima filter 42 (in FIG. 4).

Figure 14:
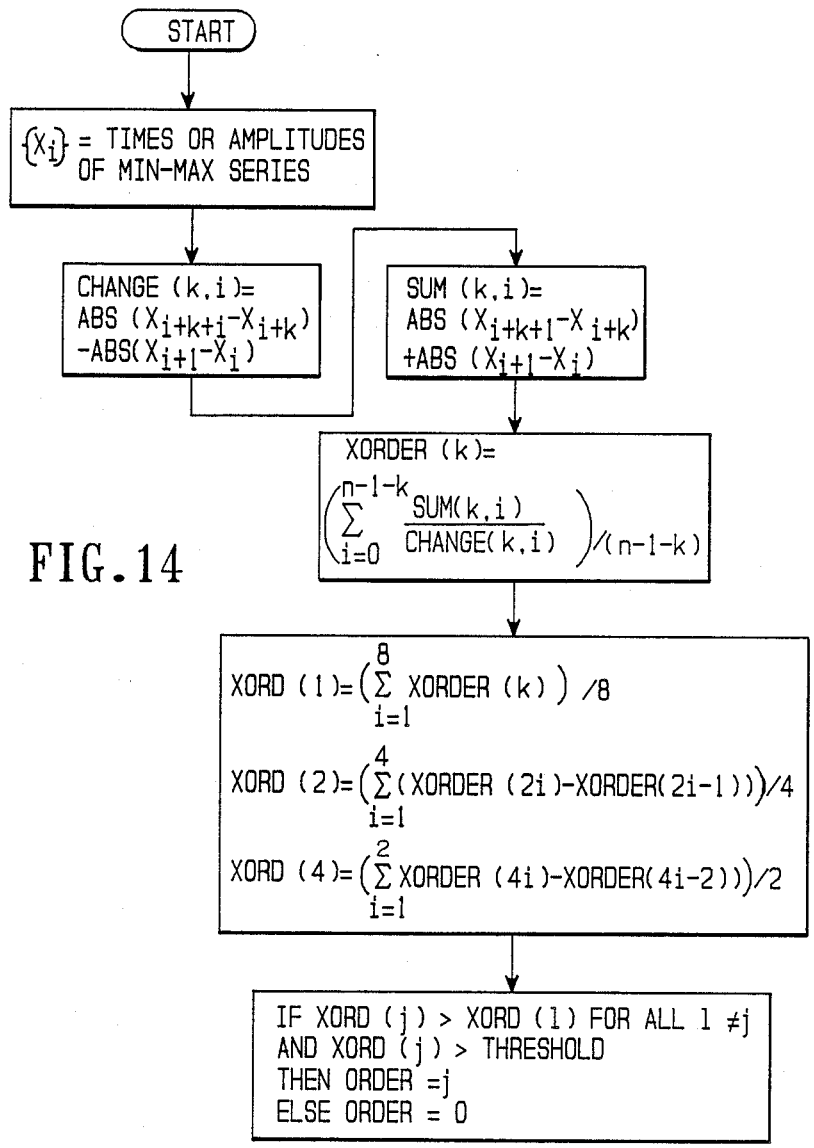
FIG. 14 is a flow chart of the processing performed in the calculation of the minima-maxima order statistic.

6. Minima-maxima order statistic (step 188): A flow chart of the minima-maxima order statistic is shown in FIG. 14.

An order of zero means the peaks are random frequently indicates ventricular fibrillation. An order of one means the pattern of the peaks is repeated with every peak. An order of two means the pattern of the peaks is repeated every two peaks, etc.

7. Derivative spikes (step 189): The derivative spikes computation determines the existence of spikes in the derivative of the ECG sample.

8. Derivative minima-maxima rate and order (step 190): The computations measure the time rate of the minima and the maxima and also computes an order statistic for them.

9. 9-slice index (step 191): As described in connection with FIG. 9, the 9-slice index is a time order statistic representing the most ordered of nine separate levels within the most recent ECG sample.

In one embodiment, nine "no-treat" tests, other than the noise and asystole tests, are executed.

Figure 10A:
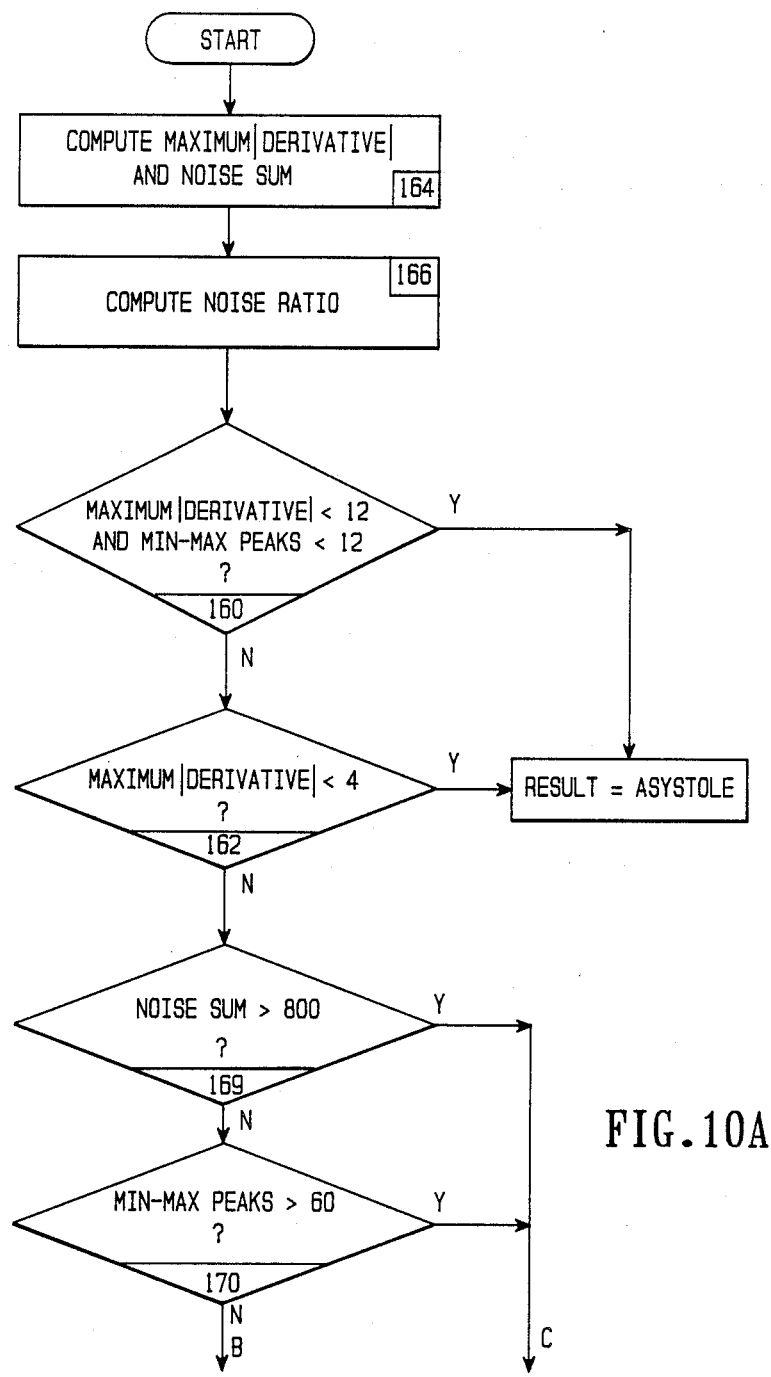
FIGS. 10A through 10D are a flow chart of the processing performed by the ANALYZING function.
Figure 10B:
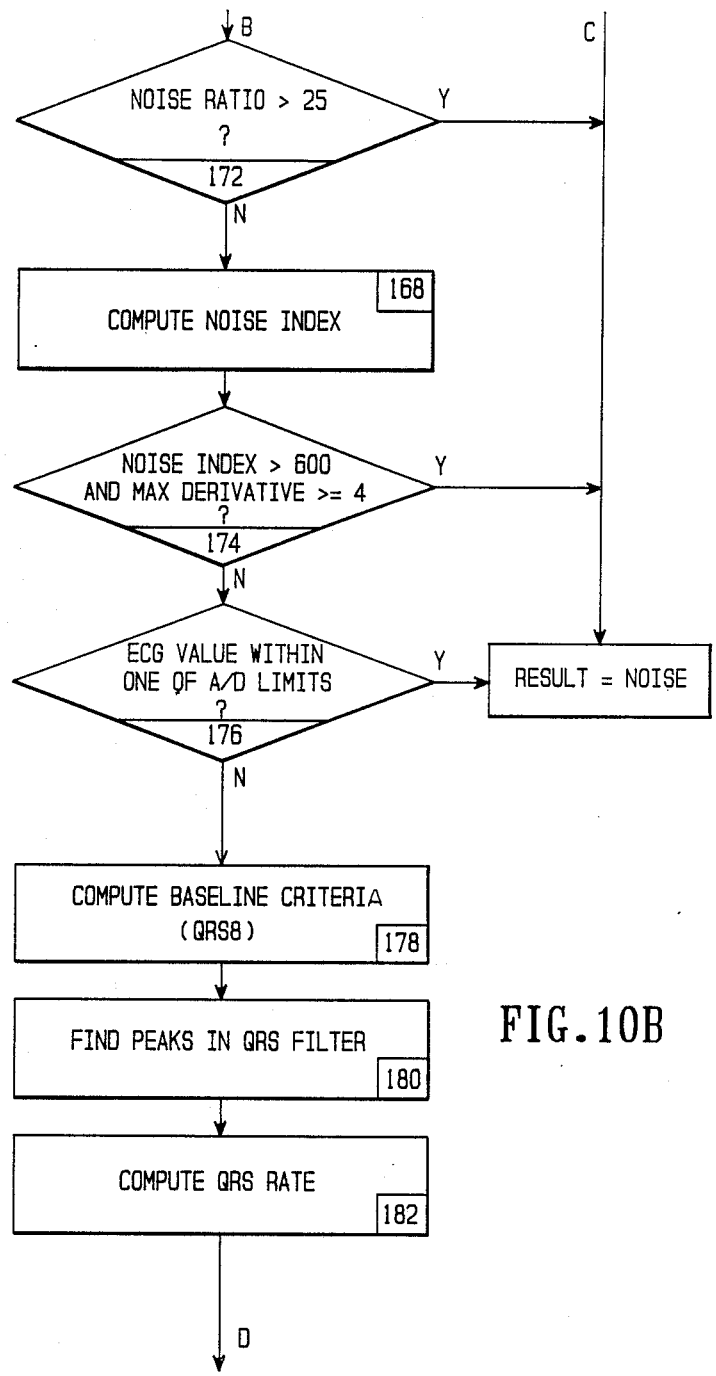
Figure 10C:
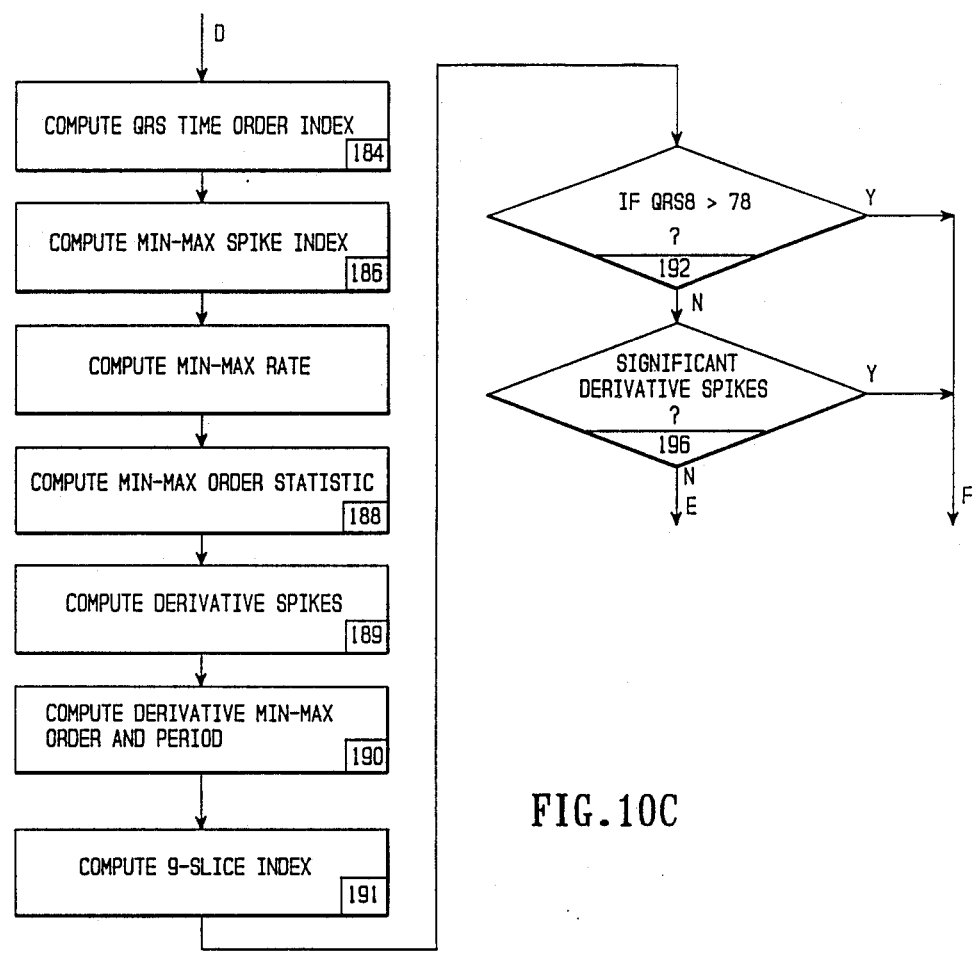
Figure 10D:
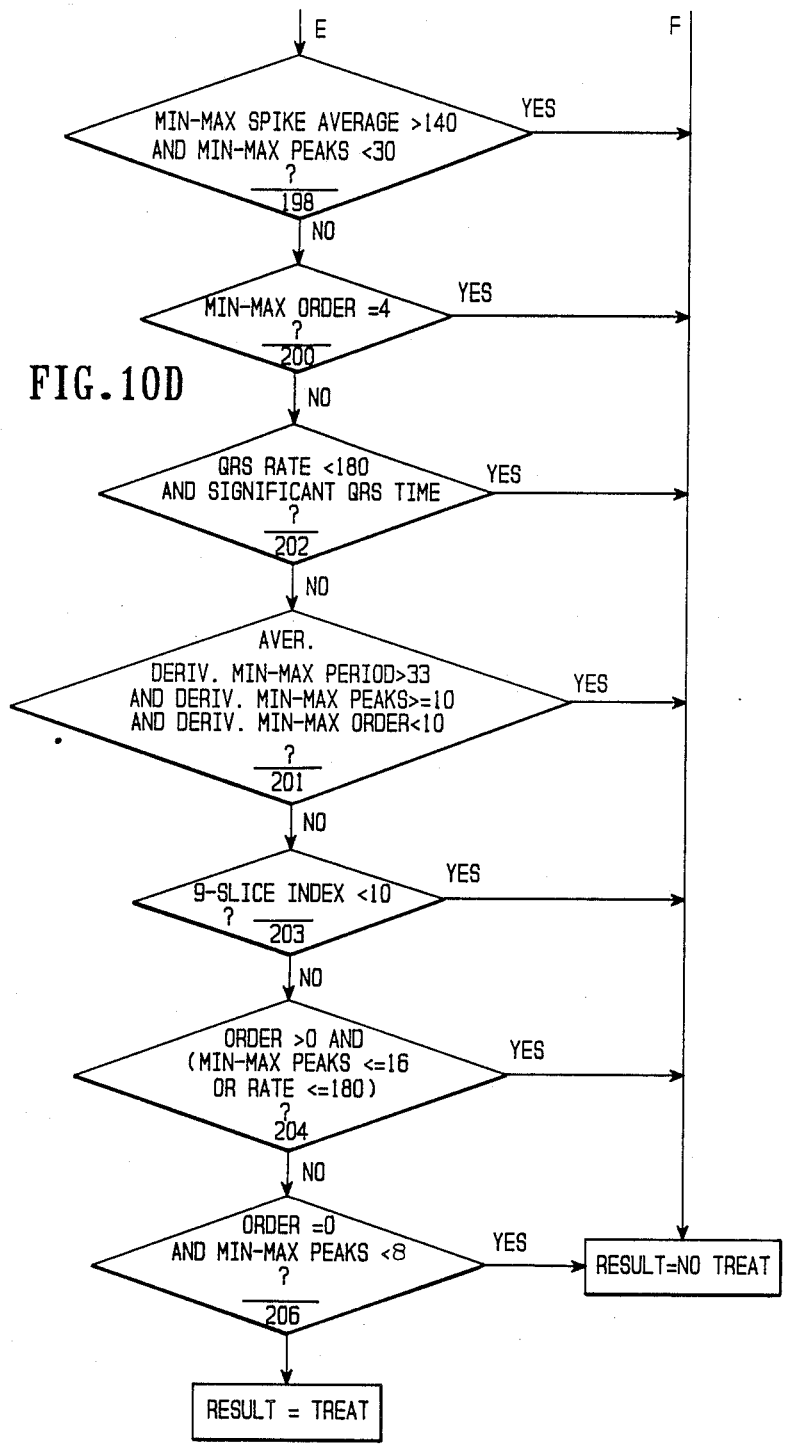

The first test is the baseline criterion of the QRS filter 48 (step 192 in FIG. 10C). Large baseline criterion values tend to signify the presence of QRS pulses, and thus, the presence of a no-treat condition. In one embodiment, the baseline criterion tests is as follows:

1. QRS8>78 (step 192)

When more than 78 of the 300 output values of the QRS filter are less than one eighth the maximum value output from QRS filter 48, the patient should not be treated with a defibrillator.

2. (Step 196) Significant number of derivative spikes. This third no-treat test examines the spikes in the derivative minima-maxima filter 42. A narrow derivative spike tends to indicate a short time between rising and falling slopes. The narrower the spike, the greater the probability that the sample is a QRS pulse. In one embodiment, the number of derivative spikes is significant if any of three conditions are present:

a. the number of spikes having a duration less than or equal to 0.03 second$\geq$1;

b. the number of spikes having a duration less than or equal to 0.04 second$\geq$2 and the number of minima-maxima peaks is less than 35; or c. QRS8 multiplied by the number of spikes having a duration less than or equal to 0.05 second is greater than 90, and either (i) the number of minima-maxima peaks is less than 24 or (ii) the number of minima-maxima peaks is less than or equal to 32 and their order equals zero.

3. (Step 198 in FIG. 10D) Minima-maxima spike average exceeds 140 and number of minima-maxima peaks is less than 30. This test checks for narrow peak transitions to detect QRS pulses.

4. Minima-maxima order=4. The fourth "no-treat" test checks the pattern of the minimum and maximum peaks to signify a no-treat condition for large P or T waves (step 200).

5. (Step 202) QRS rate is less than 180 and significant QRS time order. In one embodiment, a significant QRS time order is present when (i) the QRS rate is less than 20 times (number of QRS peaks+2), (ii) the number of QRS peaks multiplied by an index exceeds 75, where the index is the QRS time order index for determining whether the peaks are equally spaced, and (iii) the number of QRS peaks is greater than or equal to 6.

6. (Step 201) A test having three parts which must all be satisfied. The average derivative minima-maxima period must exceed 33, the derivative minima-maxima peaks must be greater than or equal to 10, and the derivative minima-maxima order must be less than 10. This test checks for ordered ECGs at rates less than 180 bpm.

7. (step 203) 9-slice index is less than 10. This test determines that there is order at a rate less than approximately 180 bpm in at least one of the slices taken in the current ECG sample.

8. (Step 204) The minima-maxima order is greater than zero and either the number of minima-maxima peaks is less than or equal to 16 or the rate is less than or equal to 180.

When minima-maxima order is greater than 0, a pattern exists in the ECG signal, indicating that the patient should not be treated unless the rhythm is a high frequency ventricular tachycardia. Testing the number of peaks and rate rules out this possibility.

9. (Step 206) The minima-maxima order equals zero and the number of minima-maxima peaks is less than eight. This ninth test checks for irregular low frequency wander.

A minima-maxima order of zero means the ECG signal is random. The number of peaks is compared to eight to check for low frequencies.

VOTING FUNCTION

The VOTING function is executed following the ANALYZING function. The voting which is performed depends on which of two modes the interpreter is in. In one mode, the monitoring mode, the VOTING function is performed on the most recent result of the ANALYZING function and a predetermined number of the preceding results. The interpreter is in the monitoring mode by default. If the result of the VOTING function is to determine that the patient is in a treatable condition, the interpreter will issue a "Check Patient" indication. Each time the interpreter determines a treatable condition when it is in the monitoring mode, this "Check Patient" indication is issued. In one embodiment, the VOTING function is accomplished by interpreting the results of the last four ANALYZING functions. If three of the last four results indicate a treat condition, the vote is to indicate a "Check Patient" message; otherwise, no indication is given.

The interpreter may alternatively be in the treating mode. It enters the treating mode when the operator presses an ANALYZE button in controls 35. The interpreter remains in the treating mode until either the patient is treated by the defibrillator or the capacitor is discharged internally. When the interpreter leaves the treating mode, it enters the monitoring mode. In one embodiment, a current result and the results of up to the prior two periods are polled to determine an ECG interpreter output decision. If two no-treat results are present, the ECG interpreter output is "no-treat." If two noise results are present, the ECG interpreter output is "noise." If two treat results are present, the ECG interpreter output is "treat." If one noise vote is present, it is processed as a no-treat result, such that one noise result and one or more no-treat results cause the ECG interpreter output to be "no-treat."

In an automatic defibrillator embodiment, the ECG interpreter output for a treat condition is converted into a signal that causes the defibrillator to treat the patient with a defibrillator voltage. In a semiautomatic defibrillator embodiment, the ECG interpreter output is a message designating the results of the operation of the ECG interpreter.

While a preferred embodiment of this invention has been described, the invention is capable of modification and addition without departing from its basic principles. Accordingly, the invention is not intended to be limited to the exact embodiment illustrated, which is presented only as an example. The scope of the invention should be determined by reference to the claims and their equivalents, interpreted in light of the prior art.

I claim:

1. A system for detecting ventricular fibrillation and high rate ventricular tachycardia in a single-channel electrocardiogram produced in a pair of electrodes connected to a patient, comprising:
   input means for receiving a sequence of digitized ECG samples of the ECG;
   storage means for storing the sequence of digitized ECG samples received through the input means;
   processing means for analyzing said sequence of ECG samples to discriminate among (1) noise, (2) ventricular fibrillation or high rate ventricular tachycardia that should be defibrillated, and (3) QRS peaks associated with ventricular contraction that should not be defibrillated; and
   output means connected to the processing means for indicating when the processing means detects ventricular fibrillation or high rate ventricular tachycardia.

2. The system of claim 1 wherein the processing means comprises:
   a microprocessor connected to the storage means, the microprocessor operable to execute a program for initializing the storage means, for performing digital filtering operations and analyzing the stored sequence of digitized ECG samples to produce analyzed ECG results, and for performing a voting operation among the analyzed ECG results, to cause the output means to indicate the detection of ventricular fibrillation or high rate ventricular tachycardia.

3. The system of claim 2 wherein the program executed by the microprocessor includes digital noise detection, noise reduction, and derivative filtering operations.

4. The system of claim 3 wherein the program executed by the microprocessor further includes a QRS digital filter for performing a moving window averaging operation on the absolute value of the output of the derivative filtering operation.

5. The system of claim 3 wherein the program executed by the microprocessor further includes operations for detecting derivative maxima and minima and a minima-maxima spike index in a stored sequence of digitally filtered ECG samples.

6. The system of claim 2 wherein the program executed by the microprocessor further includes a minima-maxima digital filter that detects the times of occurrence and values of significant local extrema in the stored sequence of digitally filtered ECG samples by defining a sequence of variable thresholds, each dependent upon the values of the two last-detected extrema, the crossing of the threshold by the values of the stored digitally filtered ECG samples signifying the detection of the next extremum.

7. The system of claim 2 wherein the program executed by the microprocessor further includes operations for detecting whether the sequence of digitally filtered ECG samples crosses a particular value defined between the maximum and minimum values attained by the digitally filtered ECG samples substantially periodically.

8. The system of claim 2 wherein the program executed by the microprocessor further includes an operation for detecting the time order of the cross points of the digitally filtered ECG samples, through one or more amplitude levels.

9. The system of claim 2 wherein the program executed by the microprocessor further includes operations for detecting peaks in the sequence of digitally filtered ECG samples, in which the peaks are detected by crossing threshold levels, the threshold levels being reduced with time, thereby making them more likely to detect reduced amplitude signals.

10. The system of claim 2 wherein the program executed by the microprocessor further includes operations for detecting the presence of noise in the stored sequence of digitized ECG samples, including detection of noise by a digital filtering operation, calculation of noise sum, noise ratio, and noise index variables, and comparison of these variables to predetermined respective thresholds.

11. A system for indicating whether to treat a patient with a defibrillator, comprising:
   input means for receiving a sequence of digitally-filtered electrocardiogram (ECG) samples of a single-channel ECG produced in a pair of electrodes connected to the patient;
   storage means for storing the sequence of digitally-filtered ECG samples received through the input means;
   processing means for analyzing said sequence of ECG samples to discriminate among (1) noise, (2) ventricular fibrillation or high rate ventricular tachycardia that should be defibrillated, and (3) QRS peaks associated with ventricular contraction that should not be defibrillated; and
   output means connected to the processing means for indicating not to treat the patient when the processing means discriminates noise or QRS peaks associated with ventricular contraction that should not be treated and for indicating to treat the patient when the processing means discriminates ventricular fibrillation or high rate ventricular tachycardia that should be treated.

12. The system of claim 11 wherein the processing means tests the sequence of digitally-filtered ECG samples periodically to derive a result for signifying the discrimination of ventricular fibrillation and high rate ventricular tachycardia.

13. The system of claim 12 wherein the processing means further compares the result of testing a sequence of digitally-filtered ECG samples with the results of testing up to two of the immediately previous sequences of digitally-filtered ECG samples received;
   and wherein the output means further indicates noise when two testing results signify noise, indicates not to treat the patient when one result signifies noise and another result signifies a no-treat condition, indicates not to treat the patient when two results signify a no-treat condition, and indicates to treat the patient when two result signify the discrimination of ventricular fibrillation or ventricular tachycardia.

14. The system of claim 13 wherein the processing means further tests each sequence of digitally-filtered ECG samples for the presence of asystole and the presence of asystole result is processed as a treat condition.

15. The system of claim 13 wherein the processing means further tests each sequence of digitally-filtered ECG samples for the presence of asystole and the presence of asystole result is processed as a no-treat condition.

16. A system for indicating whether to treat a patient with a defibrillator, comprising:
   input means for periodically receiving a sequence of digitally-filtered samples of a singlechannel electrocardiogram (ECG) produced in a pair of electrodes connected to a patient;
   storage means for storing the sequence of digital ECG samples received through the input means;
   processing means for detecting ventricular fibrillation and high rate ventricular tachycardia in the patient from said sequence of digitally-filtered ECG samples stored in the storage means, said processing means comprising:
   a microprocessor connected to the storage means, the microprocessor operable to execute a program for initializing the storage means, for performing digital filtering operations and analyzing the stored sequence of digitally-filtered ECG samples, and for voting regarding the digitally-filtered ECG samples, to discriminate among (1) noise, (2) ventricular fibrillation or high rate ventricular tachycardia that should be defibrillated, and (3) QRS peaks associated with ventricular contraction that should not be defibrillated; and
   output means connected to the processing means for indicating to treat the patient when the processing means detects heart action that should be treated, including ventricular fibrillation and high rate ventricular tachycardia.

17. The system of claim 16 wherein the program executed by the microprocessor includes digital noise detection, noise reduction, and derivative filtering operations.

18. The system of claim 17 wherein the program executed by the microprocessor further includes a QRS digital filter for performing a moving window averaging operation on the absolute value of the output of the derivative filtering operation.

19. The system of claim 18 wherein the program executed by the microprocessor further includes operations for detecting derivative maxima and minima and a minima-maxima spike index in a stored sequence of digitally filtered ECG samples.

20. The system of claim 17 wherein the program executed by the microprocessor further includes operations for detecting the presence of noise in the stored sequence of digitized ECG samples, including detection of noise by a digital filtering operation, calculation of noise sum, noise ratio, and noise index variables, and comparison of these variables to predetermined respective thresholds.

21. The system of claim 16 wherein the program executed by the microprocessor further includes a minima-maxima digital filter that detects the times of occurrence and values of significant local extrema in the stored sequence of digitally filtered ECG samples by defining a sequence of variable thresholds, each dependent upon the values of the two last-detected extrema, the crossing of the threshold by the values of the stored ECG samples signifying the detection of the next extremum.

22. The system of claim 16 wherein the program executed by the microprocessor further includes operations for detecting whether the sequence of digitally filtered ECG samples crosses a particular value defined between the maximum and minimum values attained by the digitally filtered ECG samples substantially periodically.

23. The system of claim 16 wherein the program executed by the microprocessor further includes an operation for detecting the time order of positive- and negative-going cross points, through one or more amplitude levels, of the result of a digital filtering operation.

24. The system of claim 16 wherein the program executed by the microprocessor further includes operations for detecting peaks in the sequence of digitally filtered ECG samples, in which the peaks are detected by crossing threshold levels, the threshold levels being reduced with time, thereby making them more likely to detect reduced amplitude signals.

25. The system of claim 16, further including means for generating a signal that can cause a defibrillator to treat the patient with a defibrillator voltage.

26. A data processing method for generating an output signal indicating whether to treat a patient with a defibrillator, the data processing method being implemented by processing means periodically receiving a sequence of digitally-filtered ECG samples of a single-channel of the patient's ECG signal, comprising the steps of:
  analyzing the sequence of digitally-filtered ECG samples for the occurrence of asystole;
  analyzing the sequence of digitally-filtered ECG samples for the occurrence of noise; and
  analyzing the sequence of digitally-filtered ECG samples for the occurrence of ventricular fibrillation of high rate ventricular tachycardia that should be defibrillated, or QRS peaks associated with ventricular contraction that should not be defibrillated, including low rate ventricular tachycardia.

27. The method of claim 26, further comprising the step of:
  storing a result corresponding to each sequence of digitally-filtered ECG samples, the result indicating an asystole condition when asystole is detected, indicating a no-treat condition when QRS peaks associated with ventricular contraction that should not be defibrillated is detected, a noise condition when noises is detected, and otherwise indicating a treat condition when patient heart action comprising ventricular fibrillation or high rate ventricular tachycardia is detected.

28. The method of claim 27, further comprising the steps of:
  comparing the result corresponding to the most recently received sequence of digitally-filtered ECG samples with the result from up to a first predetermined number of the sequences of digitally-filtered ECG samples received immediately prior to the most recently received sequence;
  indicating the occurrence of noise when at least a predetermined second number of noise conditions is present;
  indicating the occurrence of a treat condition when at least the predetermined second number of treat conditions is present; and
  indicating the occurrence of a no-treat condition when at least the predetermined second number of two no-treat conditions is present.

29. The method of claim 28, further comprising the step of indicating a no-treat condition when an asystole result is present.

30. The method of claim 28, further comprising the step of indicating a treat condition when an asystole result is present.

* * * * *